US008753274B2

(12) United States Patent
Ziv et al.

(10) Patent No.: US 8,753,274 B2
(45) Date of Patent: Jun. 17, 2014

(54) WIRELESS MEDICAL MONITORING SYSTEM

(75) Inventors: David Ziv, Kibbutz Baram (IL); Ilan Shopen, Kibbutz Baram (IL); Avi Keren, Kibbutz Baram (IL)

(73) Assignee: Elcam Medical Agricultural Cooperative Association, Ltd., Kibbutz Baram (IL)

( * ) Notice: Subject to any disclaimer, the term of this patent is extended or adjusted under 35 U.S.C. 154(b) by 426 days.

(21) Appl. No.: 12/307,369

(22) PCT Filed: Jul. 5, 2006

(86) PCT No.: PCT/IL2006/000781
§ 371 (c)(1), (2), (4) Date: Jan. 5, 2009

(87) PCT Pub. No.: WO2008/004205
PCT Pub. Date: Jan. 10, 2008

(65) Prior Publication Data
US 2010/0210920 A1 Aug. 19, 2010

(51) Int. Cl.

| | |
|---|---|
| ***A61B 5/00*** | (2006.01) |
| ***H04W 4/02*** | (2009.01) |
| ***H04W 84/00*** | (2009.01) |
| ***G06Q 50/22*** | (2012.01) |
| ***A61B 5/113*** | (2006.01) |
| *G06F 19/00* | (2011.01) |
| *G06Q 50/00* | (2012.01) |
| *H04W 4/00* | (2009.01) |
| *A61B 5/04* | (2006.01) |

(52) U.S. Cl.
CPC .......... *G06F 19/3418* (2013.01); *G06F 19/327* (2013.01); *G06F 19/3487* (2013.01); *H04W 4/02* (2013.01); *H04W 84/005* (2013.01); *G06Q 50/22* (2013.01); *A61B 5/113* (2013.01); *A61B 5/7435* (2013.01); *A61B 5/0002* (2013.01); *A61B 5/002* (2013.01); *A61B 5/04* (2013.01); *A61B 5/6887* (2013.01); *A61B 2505/01* (2013.01); *A61B 2505/03* (2013.01); *A61B 2505/05* (2013.01); *Y10S 128/903* (2013.01)
USPC ........... 600/301; 600/483; 600/529; 600/549; 600/323; 340/539.12; 340/1.1; 340/870.01; 340/870.16; 128/903

(58) Field of Classification Search
USPC ......... 600/300–301, 372–375, 382–385, 393, 600/481, 529, 549; 128/900, 902–906, 128/920–925; 705/2–3; 340/907, 908, 340/908.1, 909–930
See application file for complete search history.

(56) References Cited

U.S. PATENT DOCUMENTS 5,036,869 A 8/1991 Inahara (Continued)

FOREIGN PATENT DOCUMENTS

CN 2688223 Y 3/2005

(Continued)

OTHER PUBLICATIONS

An International Search Report dated Oct. 29, 2007, which issued during the prosecution of Applicant's PCT/IL06/00781.

(Continued)

*Primary Examiner* — Gary Jackson
*Assistant Examiner* — Marie Archer
(74) *Attorney, Agent, or Firm* — Stein IP, LLC

(57) ABSTRACT

An operator-controllable medical monitoring system including at least one medical sensor that is adapted to monitor at least one patient characteristic, a plurality of medical monitors, each including a monitor wireless transceiver and a medical information display and a patient companion assembly including a patient companion assembly wireless transceiver and a medical monitor selector wirelessly operative to initially select one of the plurality of medical monitors and to provide a monitor selection indication which is visually sensible to the operator.

17 Claims, 27 Drawing Sheets

D ICU 504 500 509 511 520 518 E WRONG MONITOR 500 F NEXT OK 516 522

(56) References Cited

U.S. PATENT DOCUMENTS

| | | | | |
|---|---|---|---|---|
| 5,262,944 | A * | 11/1993 | Weisner et al. | 600/300 |
| 5,375,604 | A * | 12/1994 | Kelly et al. | 600/484 |
| 5,394,882 | A | 3/1995 | Mawhinney | |
| 5,473,536 | A * | 12/1995 | Wimmer | 700/90 |
| 5,566,676 | A * | 10/1996 | Rosenfeldt et al. | 600/485 |
| 5,579,775 | A * | 12/1996 | Dempsey et al. | 600/483 |
| 5,640,953 | A * | 6/1997 | Bishop et al. | 600/300 |
| 5,752,917 | A * | 5/1998 | Fuchs | 600/484 |
| 6,093,146 | A | 7/2000 | Filangeri | |
| 6,139,503 | A | 10/2000 | Muller | |
| 6,225,901 | B1 | 5/2001 | Kail | 340/539.11 |
| 6,544,173 | B2 | 4/2003 | West et al. | |
| 6,544,174 | B2 | 4/2003 | West et al. | |
| 6,563,427 | B2 | 5/2003 | Bero et al. | 340/573.1 |
| 6,611,705 | B2 | 8/2003 | Hopman et al. | 600/509 |
| 6,705,990 | B1 | 3/2004 | Gallant et al. | |
| 6,749,566 | B2 | 6/2004 | Russ | |
| 6,801,137 | B2 | 10/2004 | Eggers | |
| 6,817,979 | B2 | 11/2004 | Nihtila | |
| 6,840,904 | B2 | 1/2005 | Goldberg | |
| 6,852,084 | B1 | 2/2005 | Boesen | |
| 7,046,961 | B2 | 5/2006 | Park | 455/41.2 |
| 7,197,357 | B2 | 3/2007 | Istvan et al. | |
| 7,231,258 | B2 | 6/2007 | Moore et al. | 607/60 |
| 7,292,164 | B1 | 11/2007 | Wegener | |
| 7,311,666 | B2 * | 12/2007 | Stupp et al. | 600/300 |
| 7,317,409 | B2 | 1/2008 | Conero | 341/127 |
| 7,327,263 | B2 | 2/2008 | Hahn et al. | 340/572.4 |
| 7,390,299 | B2 | 6/2008 | Weiner et al. | |
| 7,448,996 | B2 | 11/2008 | Khanuja et al. | |
| 7,595,723 | B2 | 9/2009 | Heitzmann et al. | 340/539.12 |
| 7,599,703 | B2 | 10/2009 | Derks et al. | 455/518 |
| 2002/0013518 | A1 * | 1/2002 | West et al. | 600/300 |
| 2002/0067269 | A1 * | 6/2002 | Cadell et al. | 340/573.1 |
| 2002/0165436 | A1 | 11/2002 | Schluter et al. | 398/135 |
| 2003/0033032 | A1 | 2/2003 | Lind et al. | 700/52 |
| 2003/0105403 | A1 | 6/2003 | Istvan et al. | |
| 2004/0073127 | A1 | 4/2004 | Istvan et al. | |
| 2004/0127802 | A1 | 7/2004 | Istvan et al. | |
| 2004/0147818 | A1 * | 7/2004 | Levy et al. | 600/300 |
| 2004/0203434 | A1 | 10/2004 | Karschnia et al. | |
| 2005/0151640 | A1 | 7/2005 | Hastings | 340/539.11 |
| 2005/0203350 | A1 | 9/2005 | Beck | |
| 2006/0247505 | A1 | 11/2006 | Siddiqui | 600/300 |
| 2007/0112274 | A1 | 5/2007 | Heitzmann et al. | |
| 2007/0270678 | A1 | 11/2007 | Fadem et al. | |
| 2008/0194925 | A1 | 8/2008 | Alsafadi et al. | |
| 2009/0099469 | A1 | 4/2009 | Flores | |
| 2009/0118596 | A1 | 5/2009 | Khanuja et al. | |

FOREIGN PATENT DOCUMENTS

| | | |
|---|---|---|
| EP | 0 381 813 | 8/1990 |
| EP | 0 601 589 | 6/1994 |
| GB | 2 258 960 | 2/1993 |
| GB | 2 271 691 | 4/1994 |
| WO | 97/18368 | 5/1997 |
| WO | 97/18639 | 5/1997 |
| WO | 01/78831 | 10/2001 |
| WO | 01/82789 | 11/2001 |
| WO | 03/043494 | 5/2003 |
| WO | 2004/072888 | 8/2004 |
| WO | 2007/058798 | 5/2007 |
| WO | WO 2008/004205 | 10/2008 |

OTHER PUBLICATIONS

An Office Action, together with the English translation, dated Jul. 24, 2013, which issued during prosecution of Chinese Patent Application No. 2009-80138737.7.

Jaap Haartsen, *Bluetooth—The Universal Radio Interface for Ad Hoc, Wireless Connectivity*, Ericsson Review No. 3, pp. 110-117, 1998.

International Search Report, dated Mar. 23, 2007, issued during prosecution of Applicant's PCT/US2006/043075.

Written Option, dated May 14, 2008, issued during prosecution of Applicant's PCT/US2006/043075.

Office Action, dated Oct. 1, 2008, issued during prosecution of U.S. Appl. No. 11/449,511.

Notice of Allowance, dated May 20, 2009, issued during prosecution of U.S. Appl. No. 11/449,511.

Letter accompanying subsequently filed items, dated Jul. 17, 2008, issued during prosecution of EP Patent App. No. 06836928.

European Search Report, dated Jun. 26, 2012, issued during prosecution of EP Patent App. No. 06766117.

Office Action, dated Jul. 24, 2012, issued during prosecution of EP Patent App. No. 06766117.

* cited by examiner

A
B
C
100
102
104
106
108
110
112
114
116
NEXT

D
E
F
ICU
ICU
ICU
A
B
C
D
WRONG MONITOR
NEXT OK
100
104
112
114
116
118
120
122

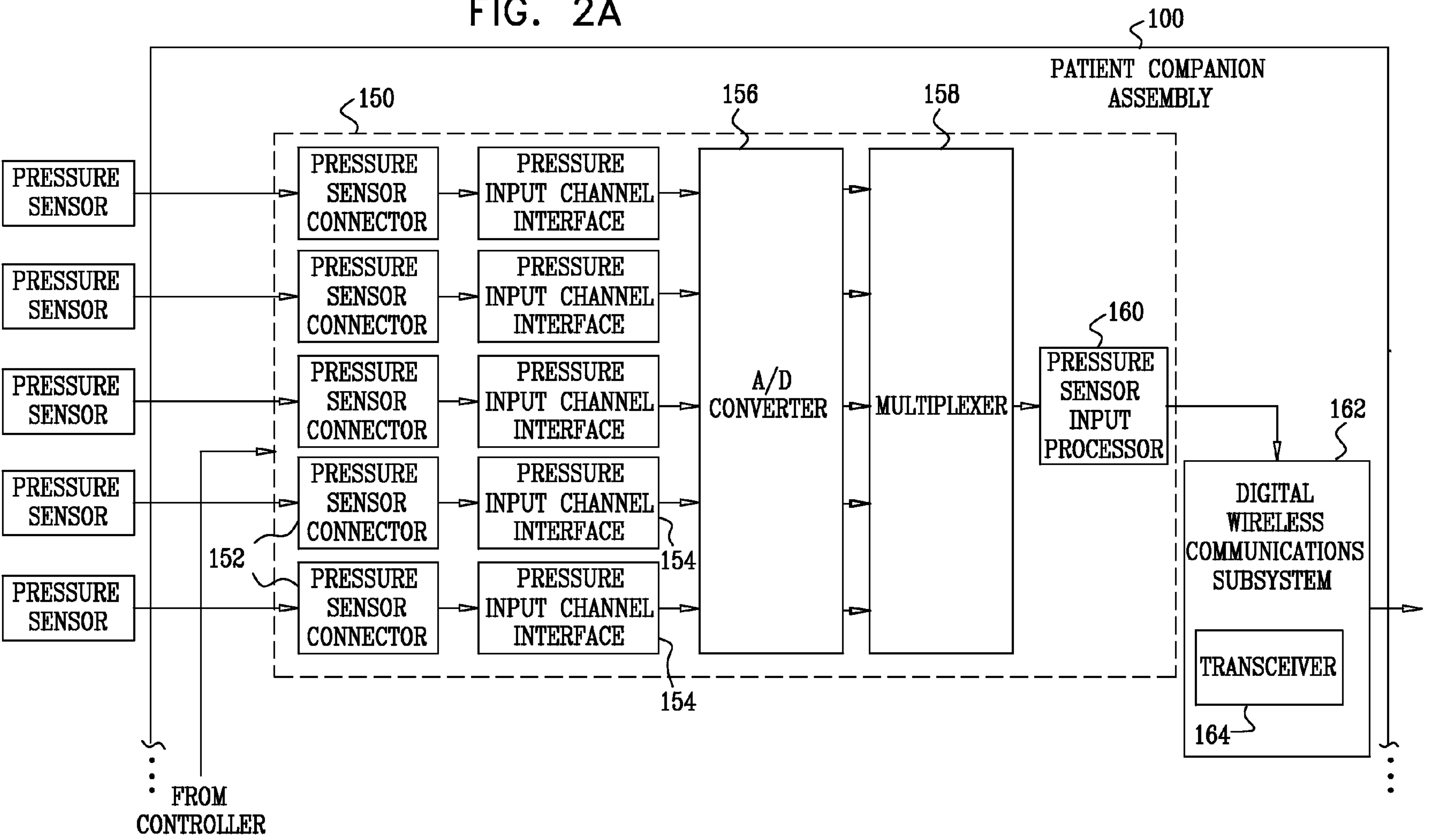
FIG. 2A
100
PATIENT COMPANION ASSEMBLY
150
PRESSURE SENSOR
PRESSURE SENSOR
PRESSURE SENSOR
PRESSURE SENSOR
PRESSURE SENSOR
PRESSURE SENSOR CONNECTOR
PRESSURE SENSOR CONNECTOR
PRESSURE SENSOR CONNECTOR
PRESSURE SENSOR CONNECTOR
PRESSURE SENSOR CONNECTOR
152
PRESSURE INPUT CHANNEL INTERFACE
PRESSURE INPUT CHANNEL INTERFACE
PRESSURE INPUT CHANNEL INTERFACE
PRESSURE INPUT CHANNEL INTERFACE
PRESSURE INPUT CHANNEL INTERFACE
154
154
156
A/D CONVERTER
158
MULTIPLEXER
160
PRESSURE SENSOR INPUT PROCESSOR
162
DIGITAL WIRELESS COMMUNICATIONS SUBSYSTEM
TRANSCEIVER
164
FROM CONTROLLER

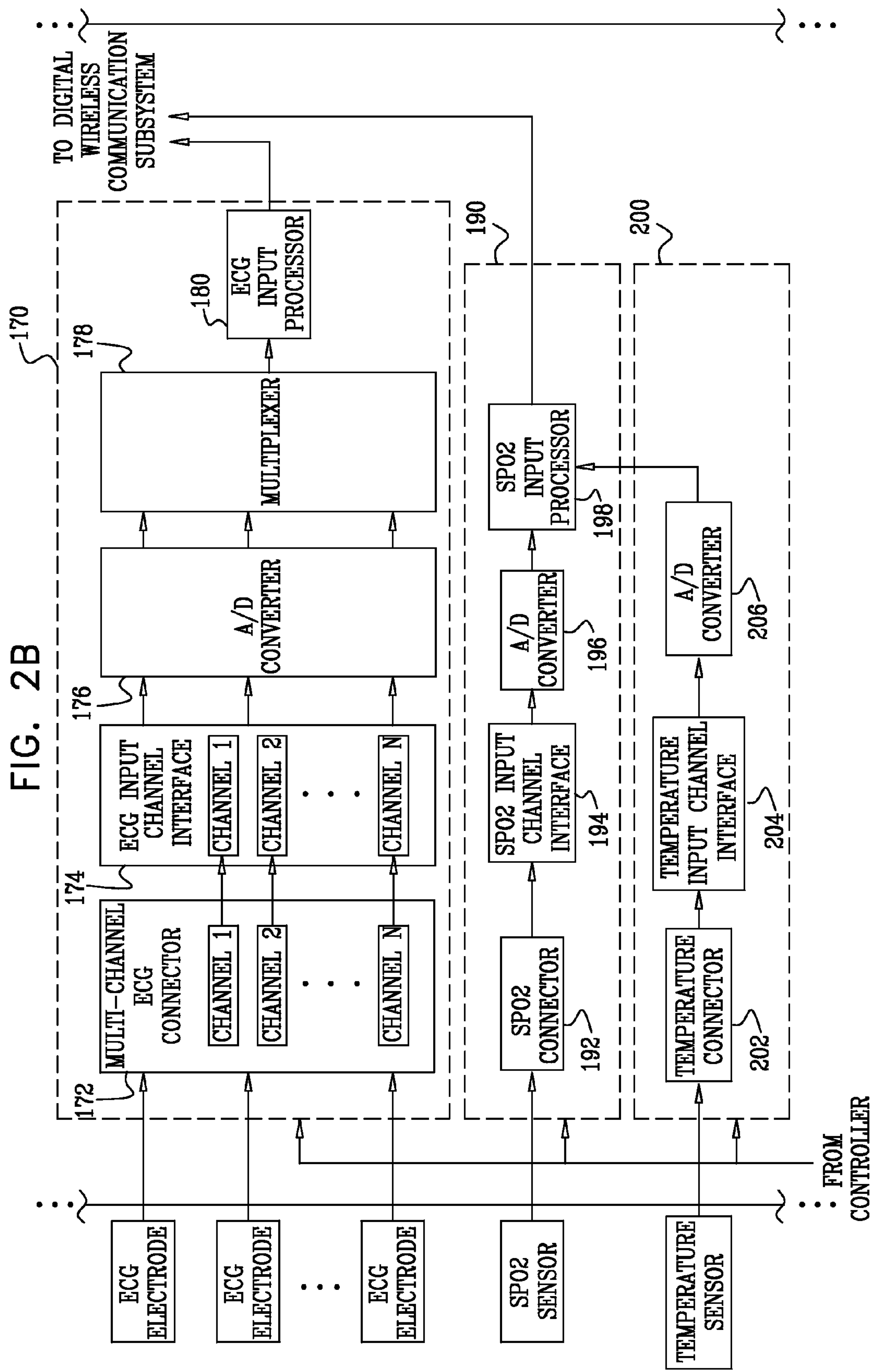
FIG. 2B
TO DIGITAL WIRELESS COMMUNICATION SUBSYSTEM
170
172
MULTI-CHANNEL ECG CONNECTOR
CHANNEL 1
CHANNEL 2
CHANNEL N
174
ECG INPUT CHANNEL INTERFACE
CHANNEL 1
CHANNEL 2
CHANNEL N
176
A/D CONVERTER
178
MULTIPLEXER
180
ECG INPUT PROCESSOR
190
192
SPO2 CONNECTOR
194
SPO2 INPUT CHANNEL INTERFACE
196
A/D CONVERTER
198
SPO2 INPUT PROCESSOR
200
202
TEMPERATURE CONNECTOR
204
TEMPERATURE INPUT CHANNEL INTERFACE
206
A/D CONVERTER
ECG ELECTRODE
ECG ELECTRODE
ECG ELECTRODE
SPO2 SENSOR
TEMPERATURE SENSOR
FROM CONTROLLER

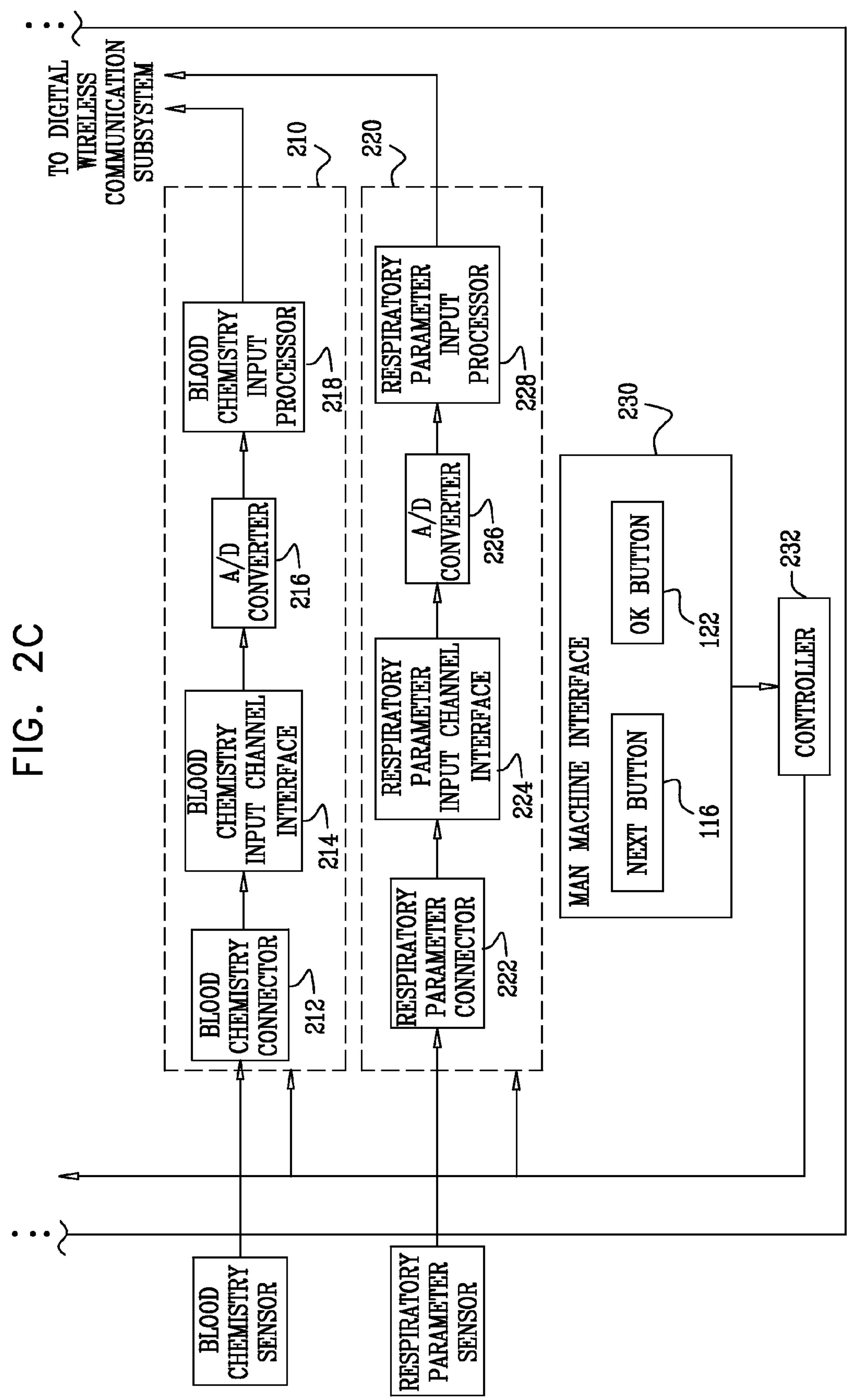
FIG. 2C
TO DIGITAL WIRELESS COMMUNICATION SUBSYSTEM
210
220
BLOOD CHEMISTRY CONNECTOR
212
BLOOD CHEMISTRY INPUT CHANNEL INTERFACE
214
A/D CONVERTER
216
BLOOD CHEMISTRY INPUT PROCESSOR
218
RESPIRATORY PARAMETER CONNECTOR
222
RESPIRATORY PARAMETER INPUT CHANNEL INTERFACE
224
A/D CONVERTER
226
RESPIRATORY PARAMETER INPUT PROCESSOR
228
MAN MACHINE INTERFACE
230
NEXT BUTTON
116
OK BUTTON
122
CONTROLLER
232
BLOOD CHEMISTRY SENSOR
RESPIRATORY PARAMETER SENSOR

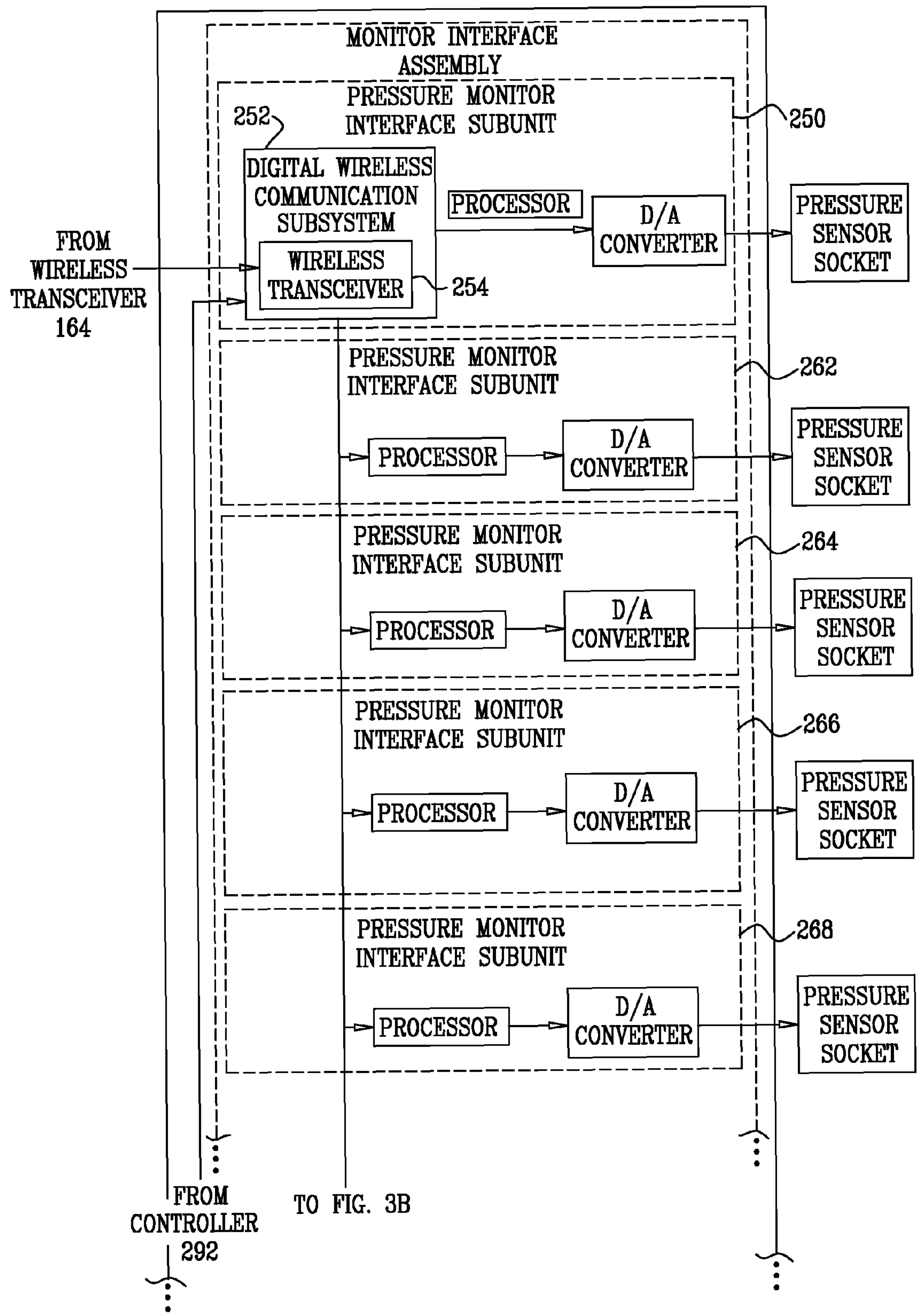

FIG. 3A
MONITOR INTERFACE ASSEMBLY
PRESSURE MONITOR INTERFACE SUBUNIT
252
DIGITAL WIRELESS COMMUNICATION SUBSYSTEM
WIRELESS TRANSCEIVER
254
PROCESSOR
D/A CONVERTER
PRESSURE SENSOR SOCKET
250
FROM WIRELESS TRANSCEIVER 164
PRESSURE MONITOR INTERFACE SUBUNIT
PROCESSOR
D/A CONVERTER
PRESSURE SENSOR SOCKET
262
PRESSURE MONITOR INTERFACE SUBUNIT
PROCESSOR
D/A CONVERTER
PRESSURE SENSOR SOCKET
264
PRESSURE MONITOR INTERFACE SUBUNIT
PROCESSOR
D/A CONVERTER
PRESSURE SENSOR SOCKET
266
PRESSURE MONITOR INTERFACE SUBUNIT
PROCESSOR
D/A CONVERTER
PRESSURE SENSOR SOCKET
268
FROM CONTROLLER 292
TO FIG. 3B

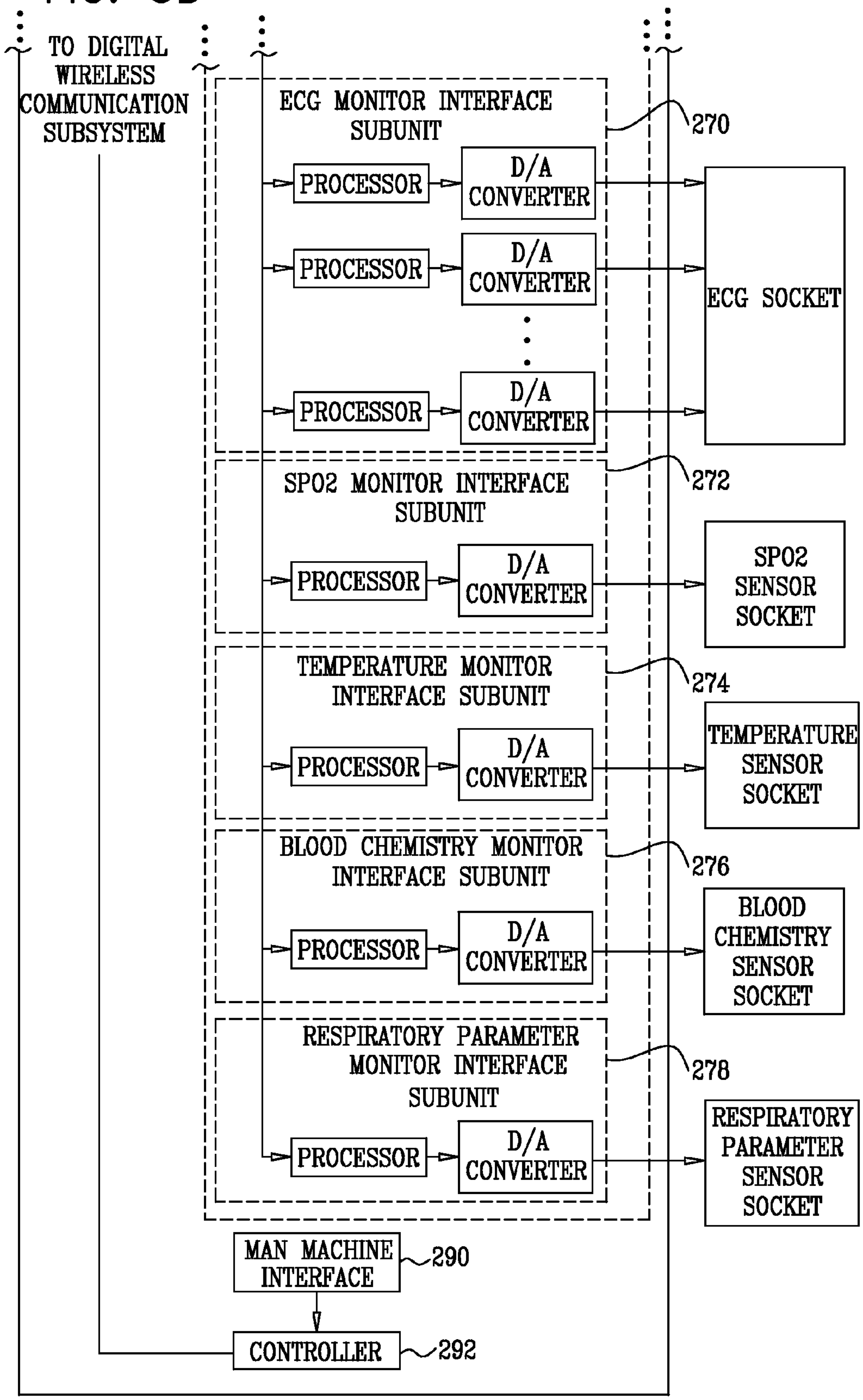
FIG. 3B
TO DIGITAL WIRELESS COMMUNICATION SUBSYSTEM
ECG MONITOR INTERFACE SUBUNIT
270
PROCESSOR
D/A CONVERTER
PROCESSOR
D/A CONVERTER
PROCESSOR
D/A CONVERTER
ECG SOCKET
SP02 MONITOR INTERFACE SUBUNIT
272
PROCESSOR
D/A CONVERTER
SP02 SENSOR SOCKET
TEMPERATURE MONITOR INTERFACE SUBUNIT
274
PROCESSOR
D/A CONVERTER
TEMPERATURE SENSOR SOCKET
BLOOD CHEMISTRY MONITOR INTERFACE SUBUNIT
276
PROCESSOR
D/A CONVERTER
BLOOD CHEMISTRY SENSOR SOCKET
RESPIRATORY PARAMETER MONITOR INTERFACE SUBUNIT
278
PROCESSOR
D/A CONVERTER
RESPIRATORY PARAMETER SENSOR SOCKET
MAN MACHINE INTERFACE
290
CONTROLLER
292

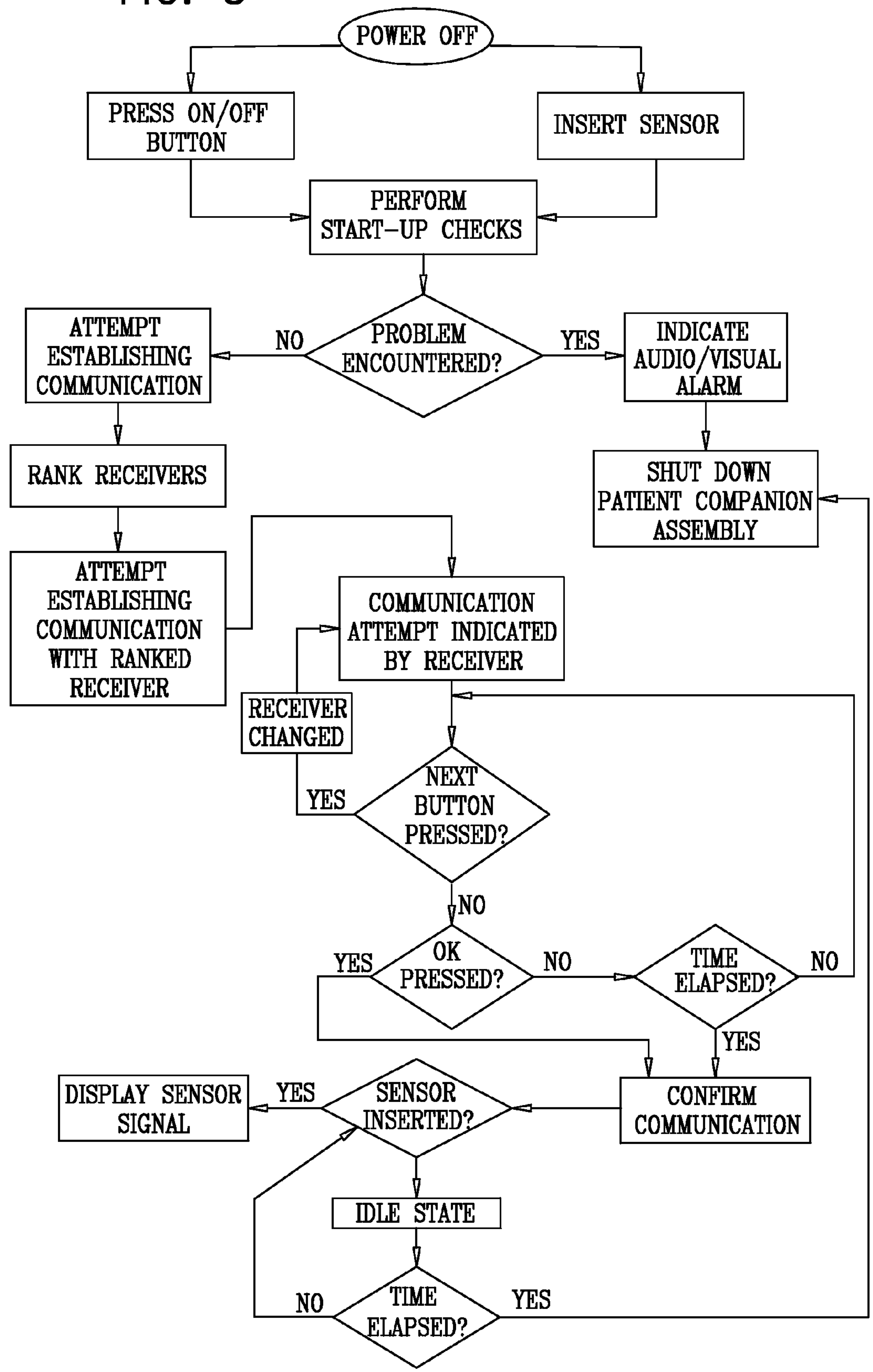
FIG. 5
POWER OFF
PRESS ON/OFF BUTTON
INSERT SENSOR
PERFORM START-UP CHECKS
PROBLEM ENCOUNTERED?
NO
YES
ATTEMPT ESTABLISHING COMMUNICATION
INDICATE AUDIO/VISUAL ALARM
RANK RECEIVERS
SHUT DOWN PATIENT COMPANION ASSEMBLY
ATTEMPT ESTABLISHING COMMUNICATION WITH RANKED RECEIVER
COMMUNICATION ATTEMPT INDICATED BY RECEIVER
RECEIVER CHANGED
YES
NEXT BUTTON PRESSED?
NO
YES
OK PRESSED?
NO
TIME ELAPSED?
NO
YES
DISPLAY SENSOR SIGNAL
YES
SENSOR INSERTED?
CONFIRM COMMUNICATION
IDLE STATE
NO
TIME ELAPSED?
YES

ICU
WRONG MONITOR
NEXT OK
A
B
C
D
D
E
F
500
504
509
511
516
518
520
522

500
PATIENT COMPANION ASSEMBLY
550
PRESSURE SENSOR INPUT RECEIVER
PRESSURE INPUT CHANNEL INTERFACE
554
552
556
A/D CONVERTER
558
MULTIPLEXER
560
PRESSURE SENSOR INPUT PROCESSOR
TO MONITOR
562
DIGITAL WIRELESS COMMUNICATIONS SUBSYSTEM
TRANSCEIVER
564
PRESSURE SENSOR
FROM CONTROLLER

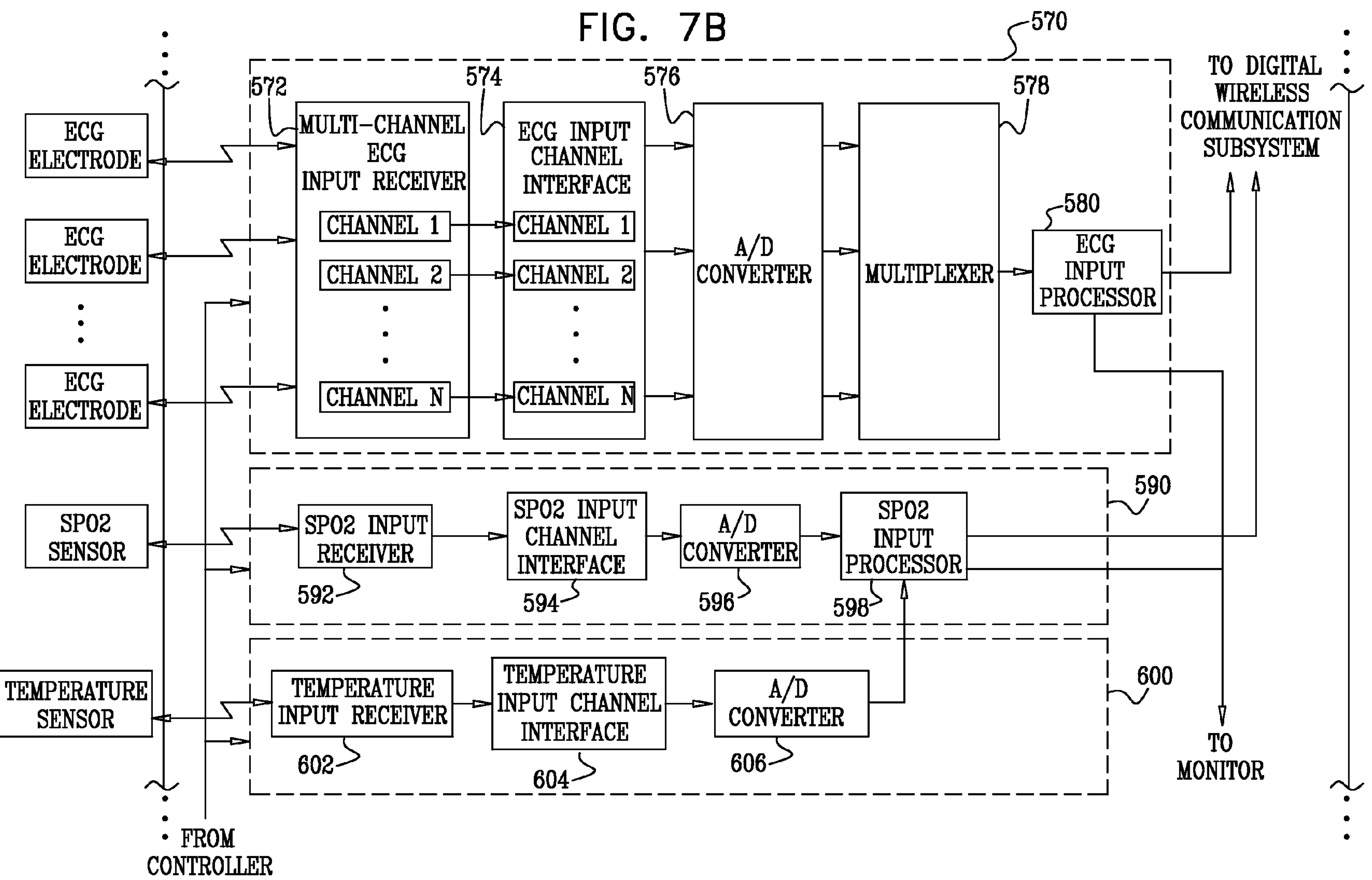
FIG. 7B
570
572
574
576
578
ECG ELECTRODE
ECG ELECTRODE
ECG ELECTRODE
MULTI-CHANNEL ECG INPUT RECEIVER
CHANNEL 1
CHANNEL 2
CHANNEL N
ECG INPUT CHANNEL INTERFACE
CHANNEL 1
CHANNEL 2
CHANNEL N
A/D CONVERTER
MULTIPLEXER
580
ECG INPUT PROCESSOR
TO DIGITAL WIRELESS COMMUNICATION SUBSYSTEM
SP02 SENSOR
SP02 INPUT RECEIVER
592
SP02 INPUT CHANNEL INTERFACE
594
A/D CONVERTER
596
SP02 INPUT PROCESSOR
598
590
TEMPERATURE SENSOR
TEMPERATURE INPUT RECEIVER
602
TEMPERATURE INPUT CHANNEL INTERFACE
604
A/D CONVERTER
606
600
TO MONITOR
FROM CONTROLLER

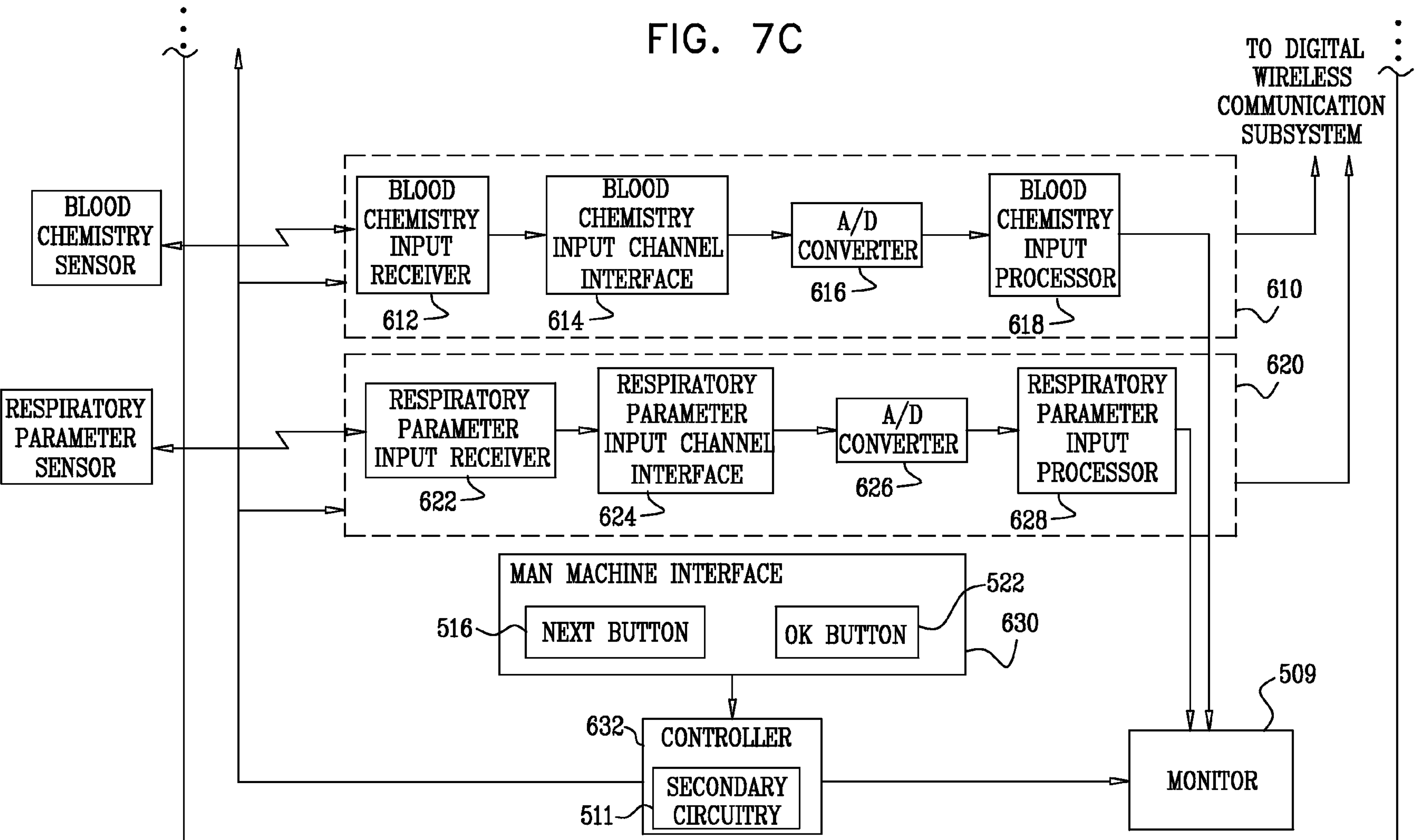
FIG. 7C
TO DIGITAL WIRELESS COMMUNICATION SUBSYSTEM
BLOOD CHEMISTRY SENSOR
BLOOD CHEMISTRY INPUT RECEIVER
612
BLOOD CHEMISTRY INPUT CHANNEL INTERFACE
614
A/D CONVERTER
616
BLOOD CHEMISTRY INPUT PROCESSOR
618
610
620
RESPIRATORY PARAMETER SENSOR
RESPIRATORY PARAMETER INPUT RECEIVER
622
RESPIRATORY PARAMETER INPUT CHANNEL INTERFACE
624
A/D CONVERTER
626
RESPIRATORY PARAMETER INPUT PROCESSOR
628
MAN MACHINE INTERFACE
516
NEXT BUTTON
OK BUTTON
522
630
509
632
CONTROLLER
SECONDARY CIRCUITRY
511
MONITOR

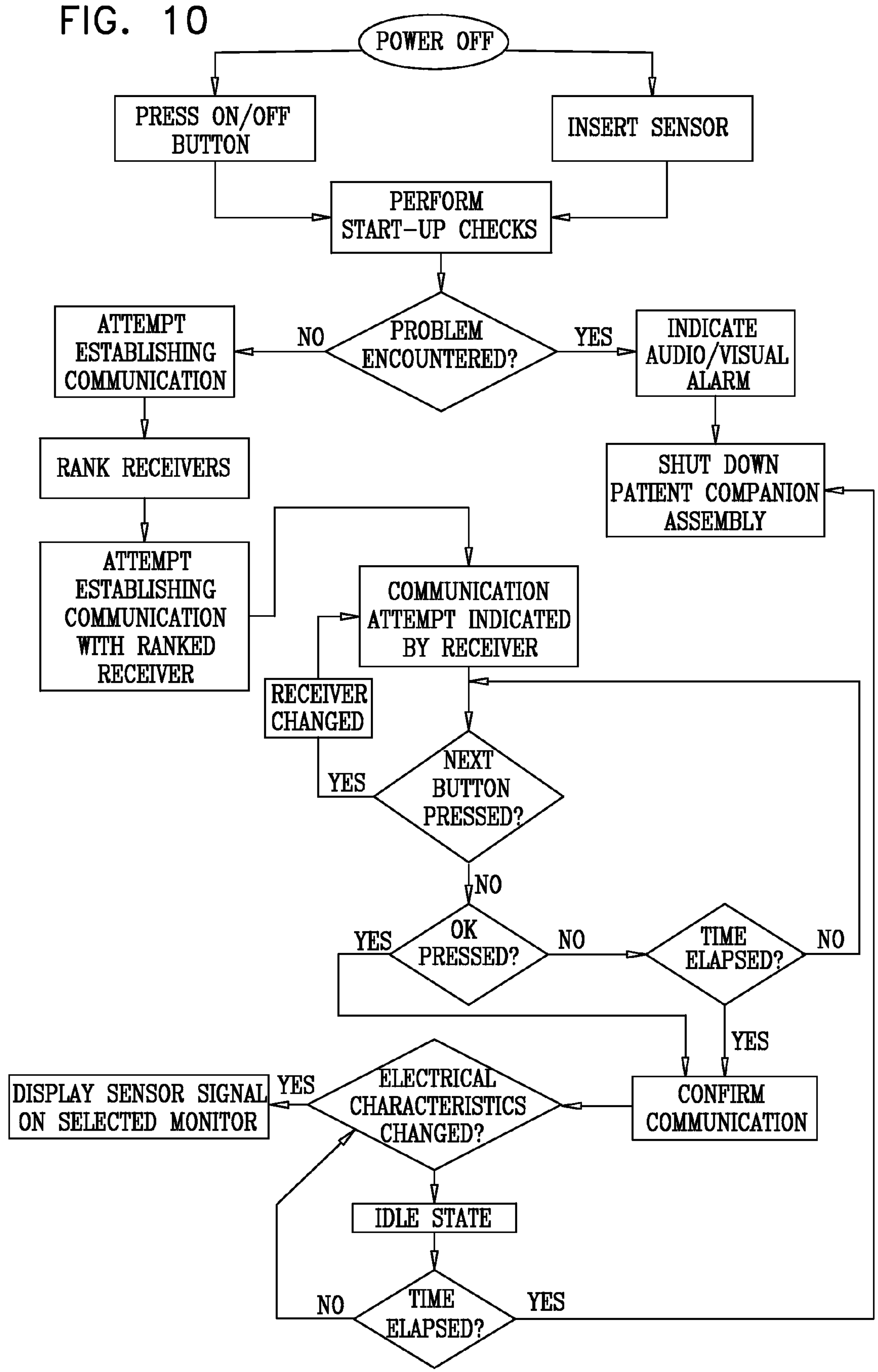
FIG. 10
POWER OFF
PRESS ON/OFF BUTTON
INSERT SENSOR
PERFORM START-UP CHECKS
PROBLEM ENCOUNTERED?
NO
YES
ATTEMPT ESTABLISHING COMMUNICATION
INDICATE AUDIO/VISUAL ALARM
RANK RECEIVERS
SHUT DOWN PATIENT COMPANION ASSEMBLY
ATTEMPT ESTABLISHING COMMUNICATION WITH RANKED RECEIVER
COMMUNICATION ATTEMPT INDICATED BY RECEIVER
RECEIVER CHANGED
YES
NEXT BUTTON PRESSED?
NO
YES
OK PRESSED?
NO
TIME ELAPSED?
NO
YES
DISPLAY SENSOR SIGNAL ON SELECTED MONITOR
YES
ELECTRICAL CHARACTERISTICS CHANGED?
CONFIRM COMMUNICATION
IDLE STATE
NO
TIME ELAPSED?
YES

A
B
C
1100
1101
1102
1104
1106
1108
1110
1113
1114
1115
1116
1117
SELECT
CANCEL

D
E
F
ICU
WRONG MONITOR
SELECTED MONITOR ABSSF
SELECTED MONITOR BBSSF
CANCEL
SELECT
1100
1104
1113
1114
1115
1116
1117
1118
1120

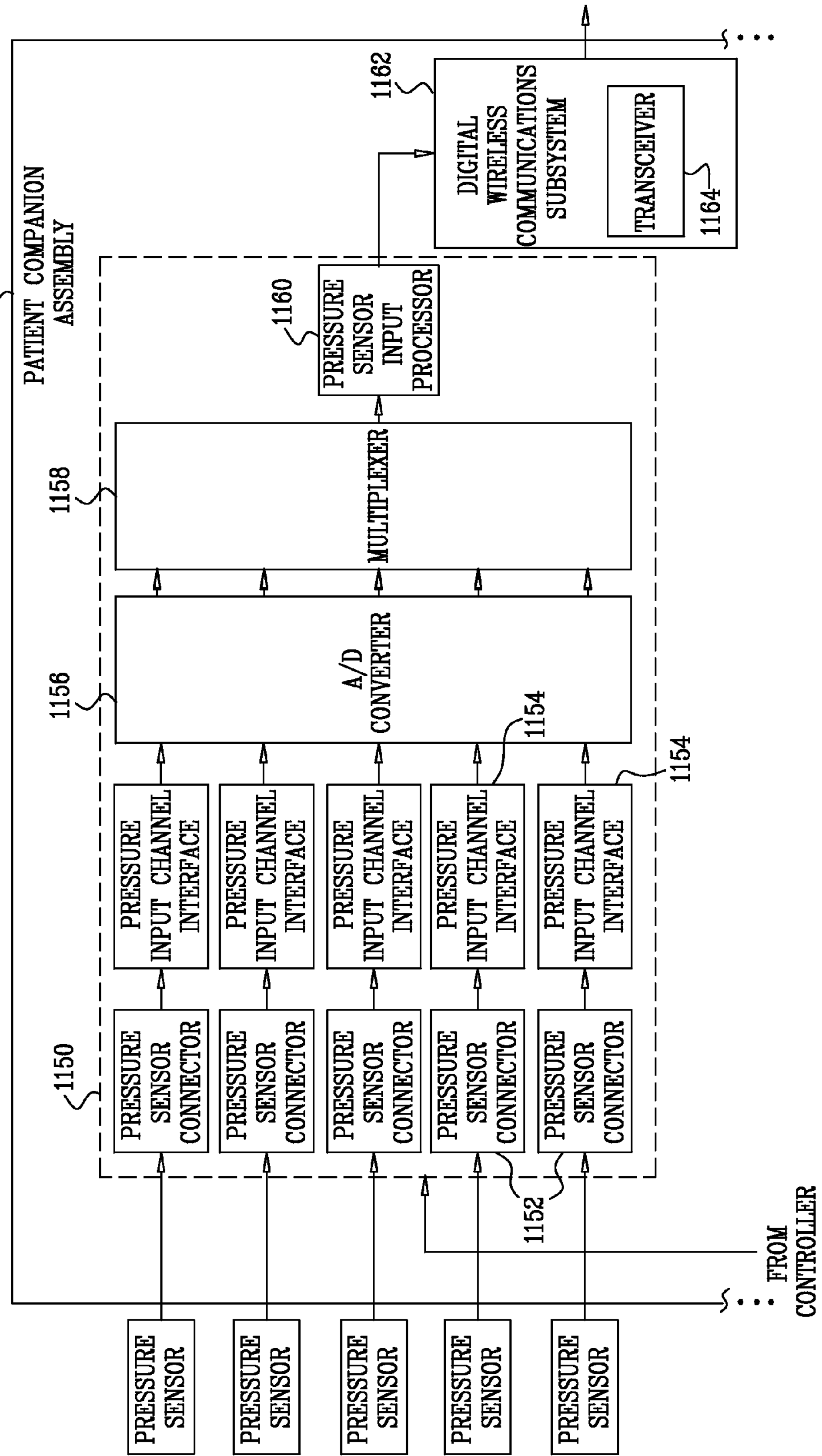
FIG. 12A
1100
PATIENT COMPANION ASSEMBLY
PRESSURE SENSOR
PRESSURE SENSOR
PRESSURE SENSOR
PRESSURE SENSOR
PRESSURE SENSOR
1150
PRESSURE SENSOR CONNECTOR
PRESSURE SENSOR CONNECTOR
PRESSURE SENSOR CONNECTOR
PRESSURE SENSOR CONNECTOR
PRESSURE SENSOR CONNECTOR
1152
PRESSURE INPUT CHANNEL INTERFACE
PRESSURE INPUT CHANNEL INTERFACE
PRESSURE INPUT CHANNEL INTERFACE
PRESSURE INPUT CHANNEL INTERFACE
PRESSURE INPUT CHANNEL INTERFACE
1154
1154
1156
A/D CONVERTER
1158
MULTIPLEXER
1160
PRESSURE SENSOR INPUT PROCESSOR
1162
DIGITAL WIRELESS COMMUNICATIONS SUBSYSTEM
TRANSCEIVER
1164
FROM CONTROLLER

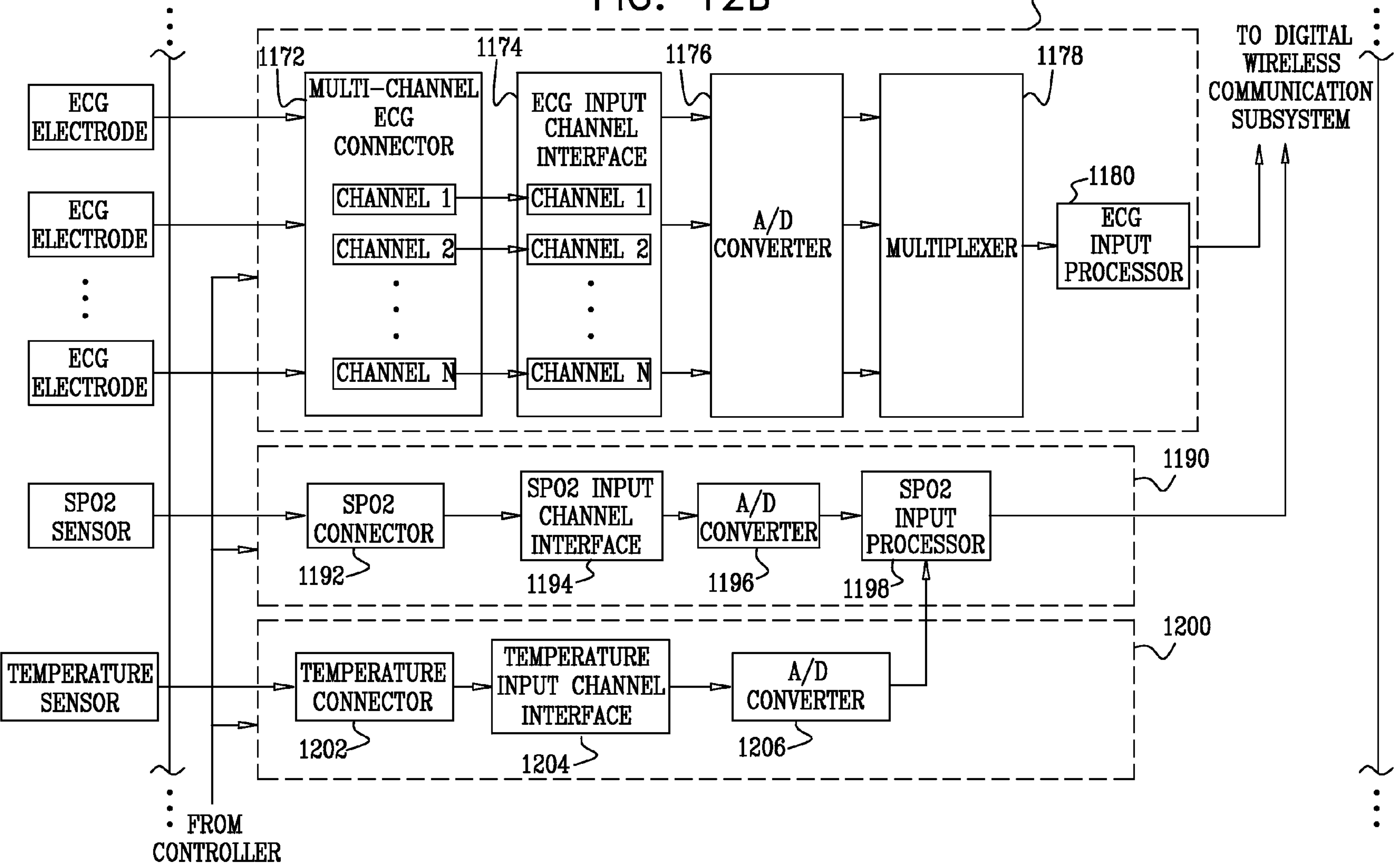
FIG. 12B
1170
1172
MULTI-CHANNEL ECG CONNECTOR
CHANNEL 1
CHANNEL 2
CHANNEL N
1174
ECG INPUT CHANNEL INTERFACE
CHANNEL 1
CHANNEL 2
CHANNEL N
1176
A/D CONVERTER
1178
MULTIPLEXER
1180
ECG INPUT PROCESSOR
TO DIGITAL WIRELESS COMMUNICATION SUBSYSTEM
ECG ELECTRODE
ECG ELECTRODE
ECG ELECTRODE
SP02 SENSOR
SP02 CONNECTOR
1192
SP02 INPUT CHANNEL INTERFACE
1194
A/D CONVERTER
1196
SP02 INPUT PROCESSOR
1198
1190
TEMPERATURE SENSOR
TEMPERATURE CONNECTOR
1202
TEMPERATURE INPUT CHANNEL INTERFACE
1204
A/D CONVERTER
1206
1200
FROM CONTROLLER

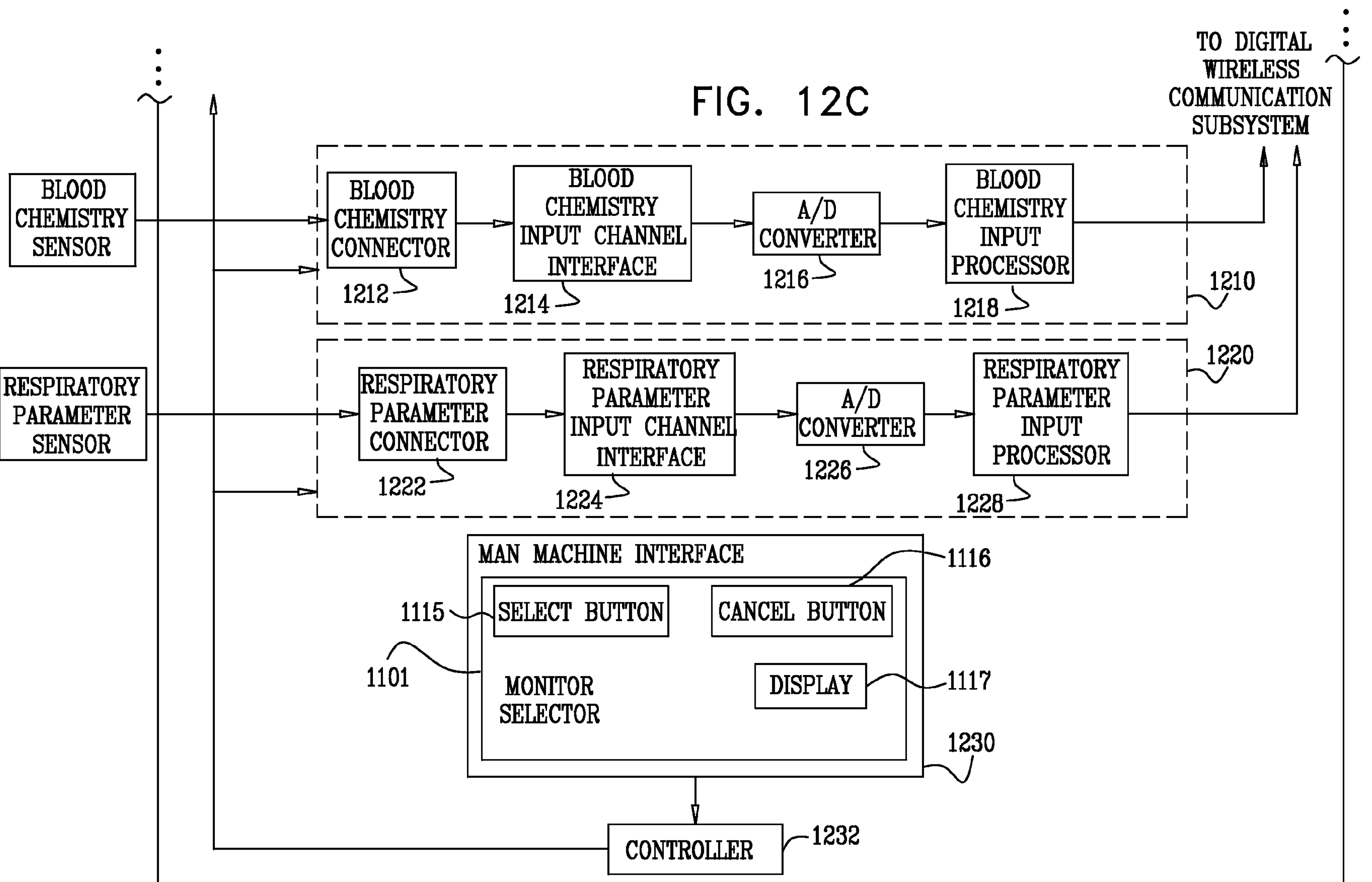
FIG. 12C
TO DIGITAL WIRELESS COMMUNICATION SUBSYSTEM
BLOOD CHEMISTRY SENSOR
BLOOD CHEMISTRY CONNECTOR
1212
BLOOD CHEMISTRY INPUT CHANNEL INTERFACE
1214
A/D CONVERTER
1216
BLOOD CHEMISTRY INPUT PROCESSOR
1218
1210
RESPIRATORY PARAMETER SENSOR
RESPIRATORY PARAMETER CONNECTOR
1222
RESPIRATORY PARAMETER INPUT CHANNEL INTERFACE
1224
A/D CONVERTER
1226
RESPIRATORY PARAMETER INPUT PROCESSOR
1228
1220
MAN MACHINE INTERFACE
1116
1115
SELECT BUTTON
CANCEL BUTTON
1101
MONITOR SELECTOR
DISPLAY
1117
1230
CONTROLLER
1232

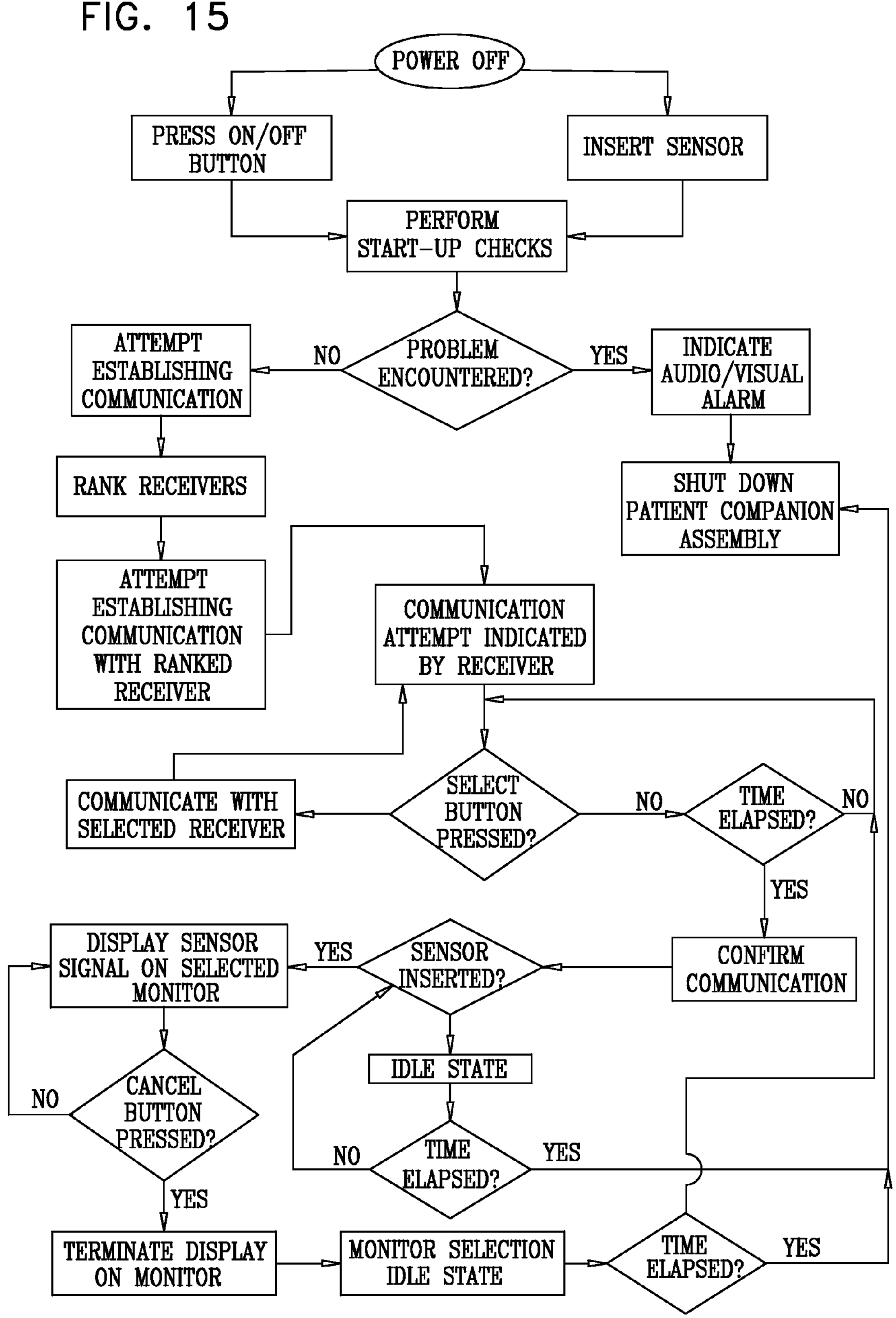
FIG. 15
POWER OFF
PRESS ON/OFF BUTTON
INSERT SENSOR
PERFORM START-UP CHECKS
PROBLEM ENCOUNTERED?
NO
YES
ATTEMPT ESTABLISHING COMMUNICATION
INDICATE AUDIO/VISUAL ALARM
RANK RECEIVERS
SHUT DOWN PATIENT COMPANION ASSEMBLY
ATTEMPT ESTABLISHING COMMUNICATION WITH RANKED RECEIVER
COMMUNICATION ATTEMPT INDICATED BY RECEIVER
COMMUNICATE WITH SELECTED RECEIVER
SELECT BUTTON PRESSED?
NO
TIME ELAPSED?
NO
YES
DISPLAY SENSOR SIGNAL ON SELECTED MONITOR
YES
SENSOR INSERTED?
CONFIRM COMMUNICATION
IDLE STATE
NO
CANCEL BUTTON PRESSED?
NO
TIME ELAPSED?
YES
YES
TERMINATE DISPLAY ON MONITOR
MONITOR SELECTION IDLE STATE
TIME ELAPSED?
YES

WIRELESS MEDICAL MONITORING SYSTEM

FIELD OF THE INVENTION

The present invention relates to medical monitoring systems, particularly to wireless medical monitoring systems.

BACKGROUND OF THE INVENTION

The following publications are believed to represent the current state of the art: U.S. Pat. Nos. 5,036,869; 5,394,882; 6,093,146; 6,544,173; 6,705,990; 6,544,174; 6,749,566; 6,801,137; 6,817,979; 6,852,084; 6,840,904 and 6,139,503; and U.S. published Patent Application Nos. 2004/0203434 and 2007/0112274.

SUMMARY OF THE INVENTION

The present invention seeks to provide a wireless medical monitoring system.

There is thus provided in accordance with a preferred embodiment of the present invention an operator-controllable medical monitoring system including at least one medical sensor that is adapted to monitor at least one patient characteristic, a plurality of medical monitors, each including a monitor wireless transceiver and a medical information display and a patient companion assembly including a patient companion assembly wireless transceiver and a medical monitor selector wirelessly operative to initially select one of the plurality of medical monitors and to provide a monitor selection indication which is visually sensible to the operator.

In accordance with a preferred embodiment of the present invention the patient companion assembly is operative automatically to establish communication between the at least one medical sensor and the initially selected one of the plurality of medical monitors absent operator intervention. Preferably, the patient companion assembly is responsive to the operator intervention to automatically select another one of the plurality of medical monitors. Additionally or alternatively, the at least one medical sensor also includes a sensor wireless transmitter which is adapted to communicate with the patient companion assembly wireless transceiver.

In accordance with another preferred embodiment of the present invention the patient companion assembly also includes sensing circuitry operative to sense changes in electrical characteristics of the operator-controllable medical monitoring system which are indicative of the activation of the at least one medical sensor, and to power up the patient companion assembly upon sensing the changes. Preferably, the changes in electrical characteristics include changes in impedance.

In accordance with yet another preferred embodiment of the present invention the patient companion assembly also includes at least one medical sensor interface subunit. Preferably, the at least one medical sensor interface subunit includes at least one of a pressure sensor interface subunit, an ECG sensor interface subunit, an SPO2 sensor interface subunit, a temperature sensor interface subunit, a blood chemistry sensor interface subunit and a respiratory parameter sensor interface subunit.

In accordance with still another preferred embodiment of the present invention the pressure sensor interface subunit includes a plurality of pressure sensor connectors, each operative to be coupled to a medical pressure sensor, a plurality of pressure input channel interfaces, each coupled to one of the plurality of pressure sensor connectors and each including an amplifier and a filter, at least one A/D converter which is operative to convert analog pressure sensor signals received from the plurality of pressure input channel interfaces to digital pressure sensor signals and a pressure sensor input processor operative to adapt the digital pressure sensor signals for digital wireless communication, and to supply the digital pressure sensor signals to the patient companion assembly wireless transceiver.

Preferably, the ECG sensor interface subunit includes a multi-channel ECG sensor connector including a plurality of channels, each of the plurality of channels being operative to be coupled to an ECG electrode, an ECG input channel interface coupled to the multi-channel ECG sensor connector and including an amplifier and a filter, at least one A/D converter which is operative to convert analog ECG signals received from the ECG input channel interface to digital ECG signals and an ECG input processor operative to adapt the digital ECG signals for digital wireless communication, and to supply the digital ECG signals to the patient companion assembly wireless transceiver.

In accordance with a further preferred embodiment of the present invention the SPO2 sensor interface subunit includes an SPO2 sensor connector operative to be coupled to an SPO2 sensor, an SPO2 input channel interface coupled to the SPO2 sensor connector and including an amplifier and a filter, an A/D converter which is operative to convert analog SPO2 sensor signals received from the SPO2 input channel interface to digital SPO2 sensor signals and an SPO2 input processor operative to adapt the digital SPO2 sensor signals for digital wireless communication, and to supply the digital SPO2 sensor signals to the patient companion assembly wireless transceiver.

In accordance with yet a further preferred embodiment of the present invention temperature sensor interface subunit includes a temperature sensor connector operative to be coupled to a temperature sensor, a temperature input channel interface coupled to the temperature sensor connector and including an amplifier and a filter and an A/D converter which is operative to convert analog temperature sensor signals received from the temperature input channel interface to digital temperature sensor signals, and to supply the digital temperature sensor signals to the patient companion assembly wireless transceiver via the SPO2 input processor.

Preferably, the blood chemistry sensor interface subunit includes at least one blood chemistry sensor connector operative to be coupled to at least one blood chemistry sensor, at least one blood chemistry input channel interface coupled to the at least one blood chemistry sensor connector and including an amplifier and a filter, an A/D converter which is operative to convert analog blood chemistry sensor signals received from the at least one blood chemistry input channel interface to digital blood chemistry sensor signals and a blood chemistry input processor operative to adapt the digital blood chemistry sensor signals for digital wireless communication, and to supply the digital blood chemistry sensor signals to the patient companion assembly wireless transceiver.

In accordance with a still further preferred embodiment of the present invention the respiratory parameter sensor interface subunit includes at least one respiratory parameter sensor connector operative to be coupled to at least one respiratory parameter sensor, at least one respiratory parameter input channel interface coupled to the at least one respiratory parameter sensor connector and including an amplifier and a filter, an A/D converter which is operative to convert analog respiratory parameter sensor signals received from the at least one respiratory parameter input channel interface to digital respiratory parameter sensor signals and a respiratory parameter input processor operative to adapt the digital respiratory parameter sensor signals for digital wireless communication, and to supply the digital respiratory parameter sensor signals to the patient companion assembly wireless transceiver.

In accordance with an additional preferred embodiment of the present invention the patient companion assembly also includes a controller operative to govern operation of the at least one medical sensor interface subunit and a man-machine interface adapted to be operated by an operator to provide inputs useful in controlling operation of the controller. Preferably, the patient companion assembly also includes at least one socket adapted to receive at least one corresponding sensor connector associated with the at least one medical sensor and power management functionality, operative, upon insertion of the at least one sensor connector to the at least one socket, to power-up the patient companion assembly. Additionally, the power management functionality is operative to shut-down the patient companion assembly if no sensor connector is connected to the at least one socket for a predetermined time duration.

In accordance with another preferred embodiment of the present invention the medical monitor selector includes a remote control device which is responsive to the operator intervention to direct an operator intervention monitor selection signal generally toward an operator selected one of the plurality of medical monitors. Preferably, the patient companion assembly also includes a patient companion assembly monitor which is one of the plurality of medical monitors. Additionally or alternatively, the at least one medical sensor includes at least one of a pressure sensor, a temperature sensor, an ECG sensor, an SPO2 sensor, a blood chemistry sensor and a respiratory parameter sensor. Preferably, the pressure sensor includes at least one of an intracranial pressure sensor, an arterial pressure sensor and a venous pressure sensor.

In accordance with still another preferred embodiment of the present invention the plurality of medical monitors each includes at least one sensor socket operative to provide electrical power obtained from the medical monitor to at least one of the monitor wireless transceiver and electrical circuitry coupled to other sensor sockets.

There is also provided in accordance with another preferred embodiment of the present invention a patient companion assembly useful in an operator-controllable medical monitoring system including at least one medical sensor that is adapted to monitor at least one patient characteristic and a plurality of medical monitors, each including a monitor wireless transceiver and a medical information display, the patient companion assembly including a patient companion assembly wireless transceiver and a medical monitor selector wirelessly operative to initially select one of the plurality of medical monitors and to provide a monitor selection indication which is visually sensible to the operator.

In accordance with a preferred embodiment of the present invention the patient companion assembly is operative automatically to establish communication between the at least one medical sensor and the initially selected one of the plurality of medical monitors absent operator intervention. Preferably, the patient companion assembly is responsive to the operator intervention to automatically select another one of the plurality of medical monitors. Additionally or alternatively, the patient companion assembly also includes sensing circuitry operative to sense changes in electrical characteristics of the operator-controllable medical monitoring system which are indicative of the activation of the at least one medical sensor, and to power up the patient companion assembly upon sensing the changes.

In accordance with another preferred embodiment of the present invention the patient companion assembly also includes at least one medical sensor interface subunit including at least one of a pressure sensor interface subunit, an ECG sensor interface subunit, an SPO2 sensor interface subunit, a temperature sensor interface subunit, a blood chemistry sensor interface subunit and a respiratory parameter sensor interface subunit. Preferably, the patient companion assembly also includes a controller operative to govern operation of the at least one medical sensor interface subunit and a man-machine interface adapted to be operated by an operator to provide inputs useful in controlling operation of the controller.

In accordance with yet another preferred embodiment of the present invention the patient companion assembly includes at least one socket adapted to receive at least one corresponding sensor connector associated with the at least one medical sensor and power management functionality, operative, upon insertion of the at least one sensor connector to the at least one socket, to power-up the patient companion assembly. Preferably, the power management functionality is operative to shut-down the patient companion assembly if no sensor connector is connected to the at least one socket for a predetermined time duration.

In accordance with still another preferred embodiment of the present invention the medical monitor selector includes a remote control device which is responsive to the operator intervention to direct an operator intervention monitor selection signal generally toward an operator selected one of the plurality of medical monitors. Preferably, the patient companion assembly also includes a patient companion assembly monitor which is one of the plurality of medical monitors.

There is further provided in accordance with a further preferred embodiment of the present invention an operator-controllable medical monitoring system including at least one medical sensor that is adapted to monitor at least one patient characteristic, a patient companion assembly including a patient companion assembly wireless transceiver and a plurality of medical monitors, each including a monitor wireless transceiver and a medical information display, the monitor wireless transceiver being powered by a source of electrical power which is also operative to power the medical information display.

In accordance with a preferred embodiment of the present invention the plurality of medical monitors each includes at least one sensor socket operative to provide the electrical power to at least one of the monitor wireless transceiver and electrical circuitry coupled to other sensor sockets.

There is additionally provided in accordance with another preferred embodiment of the present invention a method for operator-controllable medical monitoring of a patient, employing at least one medical sensor that is adapted to monitor at least one patient characteristic and a plurality of medical monitors, each including a monitor wireless transceiver and a medical information display, the method including employing a patient companion assembly, including a patient companion assembly wireless transceiver and a medical monitor selector, wirelessly to initially select one of the plurality of medical monitors and to provide a monitor selection indication which is visually sensible to the operator.

In accordance with a preferred embodiment of the present invention the method also includes employing the patient companion assembly automatically to establish communication between the at least one medical sensor and the initially selected one of the plurality of medical monitors absent operator intervention. Preferably, the method also includes employing the patient companion assembly, responsive to the operator intervention, automatically to select another one of the plurality of medical monitors. Additionally or alternatively, the method also includes employing sensing circuitry forming part of the patient companion assembly to sense changes in electrical characteristics which are indicative of the activation of the at least one medical sensor, and to power up the patient companion assembly upon sensing the changes.

In accordance with another preferred embodiment of the present invention the employing a patient companion assembly includes employing power management functionality, operative, upon insertion of at least one sensor connector to at least one socket of a monitor, to power-up the patient companion assembly. Preferably, the method also includes employing the power management functionality to shutdown the patient companion assembly if a sensor connector is not connected to the at least one socket for a predetermined time duration.

In accordance with still another preferred embodiment of the present invention the employing the patient companion assembly includes employing a remote control device which is responsive to the operator intervention to direct an operator intervention monitor selection signal generally toward an operator selected one of the plurality of medical monitors. Preferably, the method also includes providing electrical power obtained from the medical monitor to the monitor wireless transceiver.

BRIEF DESCRIPTION OF THE DRAWINGS

The present invention will be understood and appreciated more fully from the following detailed description, taken in conjunction with the drawings in which:

FIGS. 2A, 2B and 2C, taken together, form a simplified block diagram illustration of a patient companion assembly useful in the operator controlled medical monitoring system of FIGS. 1A and 1B;

FIGS. 3A and 3B, taken together, form a simplified block diagram illustration of a monitor interface assembly useful in the operator controlled medical monitoring system of FIGS. 1A and 1B;

FIG. 5 is a simplified flow chart illustration of the operation of the system of FIGS. 1A-4;

FIG. 10 is a simplified flow chart illustration of the operation of the system of FIGS. 6A-9;

FIGS. 12A, 12B and 12C, taken together, form a simplified block diagram illustration of a patient companion assembly useful in the operator controlled medical monitoring system of FIGS. 11A and 11B;

FIG. 15 is a simplified flow chart illustration of the operation of the system of FIGS. 11A-14.

DETAILED DESCRIPTION OF PREFERRED EMBODIMENTS

Figure 1A:
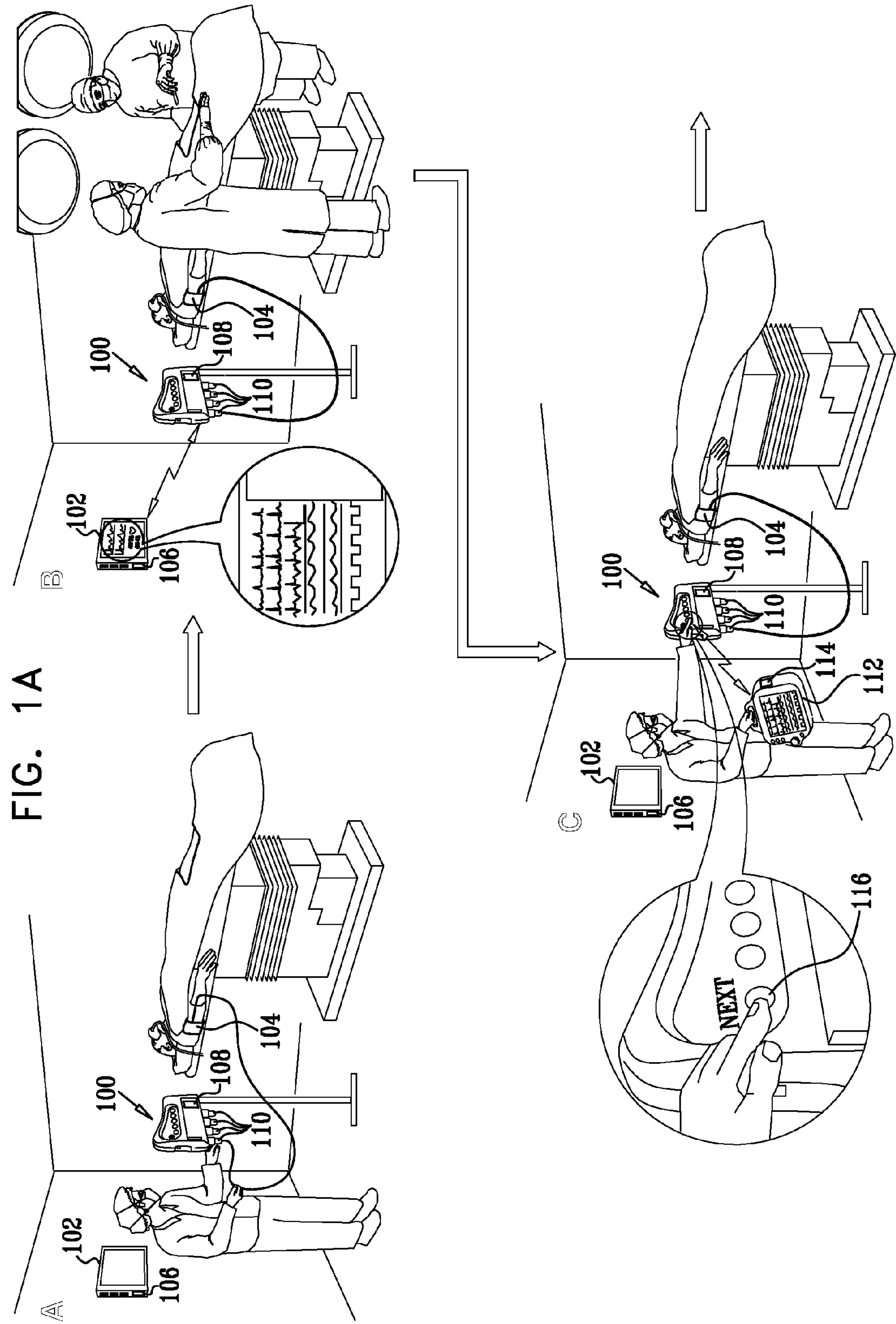
FIGS. 1A and 1B, taken together, are a simplified pictorial illustration of the operation of an operator controlled medical monitoring system constructed and operative in accordance with a preferred embodiment of the present invention.
Figure 1B:
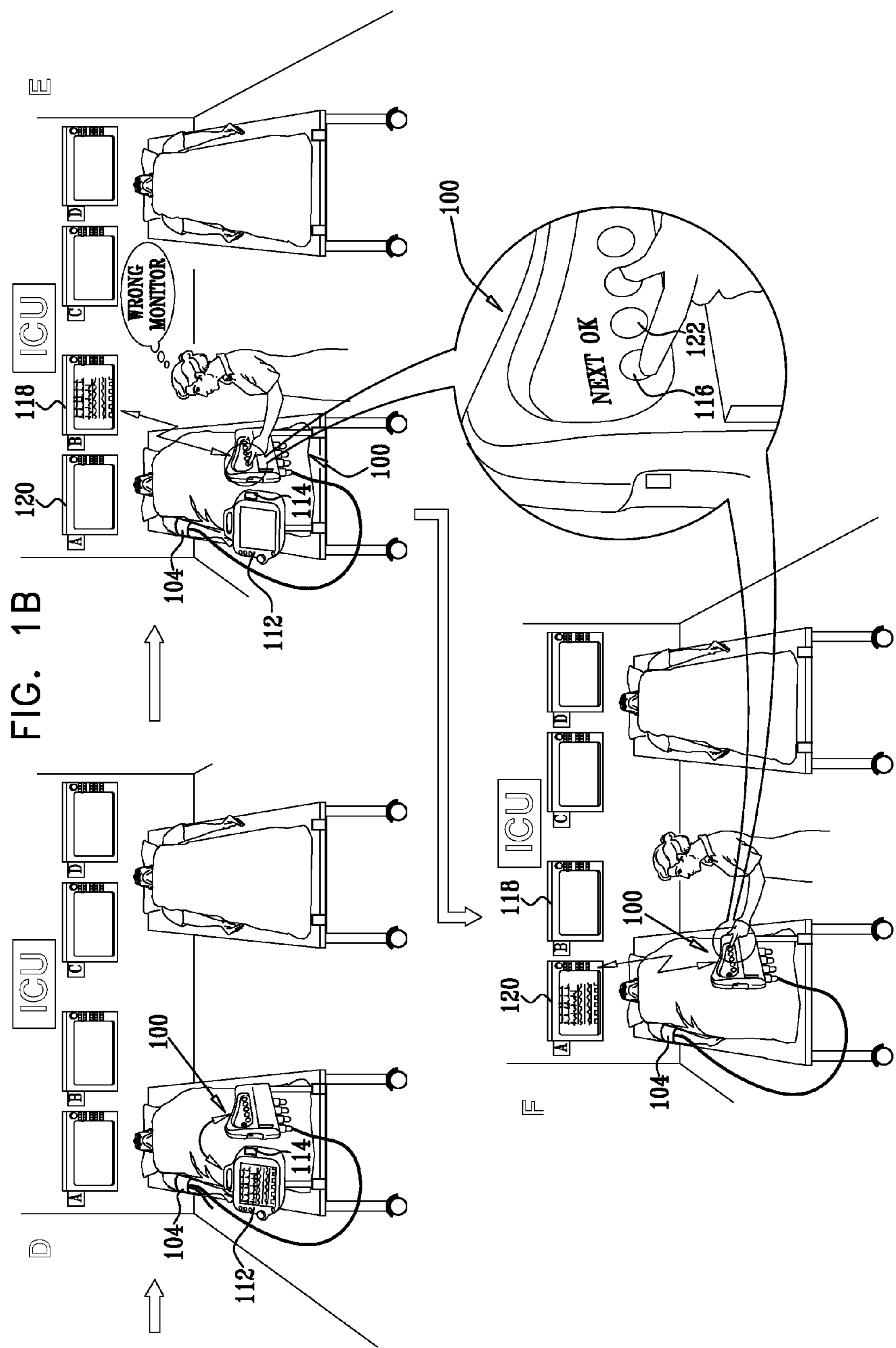

Reference is now made to FIGS. 1A and 1B, which, taken together, are a simplified pictorial illustration of the operation of a operator controlled medical monitoring system constructed and operative in accordance with a preferred embodiment of the present invention. As seen in FIGS. 1A and 1B, there is provided an operator controlled medical monitoring system including a medical sensor that is adapted to monitor a patient characteristic; a plurality of medical monitors, each including a wireless receiver and a medical information output device; and a patient companion assembly, including a medical monitor selector employed by an operator to select one of the plurality of medical monitors and to establish communication between the medical sensor and a selected one of the plurality of medical monitors.

Turning to FIG. 1A, at stage A, there is seen a patient, typically in an operating room environment. In accordance with a preferred embodiment of the present invention, the patient is coupled to a patient companion assembly 100, which includes a medical monitor selector which can be employed by an operator to select one of a plurality of medical monitors, such as a conventional medical monitor 102, and to establish communication between medical sensing devices, such as a blood pressure sensor 104, attached to the patient and the selected medical monitor, preferably via a wireless receiver 106 associated with the medical monitor 102. It is noted that in the embodiment shown in FIG. 1A, a wired connection is provided between the sensor 104 and the patient companion assembly 100, it being appreciated that alternatively a wireless connection may be provided. Preferably, the connection between the patient companion assembly 100 and the medical monitor 102 is wireless and employs a transmitter 108, preferably forming part of the patient companion assembly 100, which communicates with wireless receiver 106.

It is also appreciated that the medical sensor may be mounted on the patient, as shown in FIG. 1A, or otherwise coupled to the patient. Examples of medical sensor devices that may be coupled to the patient and mounted on the patient companion assembly 100 include physiological pressure sensors. FIG. 1A shows the operator in the process of connecting the sensor 104 to one of a plurality of connection sockets 110 of the patient companion assembly 100. Preferably, connection of a medical sensing device initiates powering up of the patient companion assembly 100.

At stage B, the patient is being operated on in the same location as that shown at stage A. It is seen that monitor 102 is displaying various patient parameters received from medical sensing devices, such as sensor 104, via the patient companion assembly 100, transmitter 108 and receiver 106.

At stage C, following the operation in Stage B, the patient is being prepared for transfer to another location and a conventional portable monitor 112, preferably having associated therewith a wireless receiver 114, is introduced. The operator is shown initializing communication between the patient companion assembly 100 and the portable monitor 112, typically by pressing a NEXT button 116 on the patient companion assembly 100. The initializing typically enables the patient parameters to appear on the portable monitor 112, as shown, and preferably simultaneously terminates display of the patient parameters on the monitor 102, also as shown.

As seen in FIG. 1B, stage D illustrates the patient following his transfer to an ICU or other recovery room, still coupled to portable monitor 112, which continues to display the patient parameters.

At stage E, initial selection of one of a plurality of wall-mounted monitors is shown. The selection is typically carried out by an operator pressing the NEXT button 116 on the patient companion assembly 100. The selection typically enables the patient parameters to appear on the selected wall-mounted monitor, here designated 118, and preferably simultaneously terminates display of the patient parameters on the portable monitor 112, also as shown.

In situations where there are plural wall-mounted monitors available for communication with the patient companion assembly 100, the selection of a wall-mounted monitor preferably is based on the strongest wireless signal sensed by the patient companion assembly 100. In the illustration at stage E, wall-mounted monitor 118 is not the wall-mounted monitor that the operator desires to employ. Accordingly, in accordance with a preferred embodiment of the present invention, and as shown at stage F, the operator can select an alternative wall-mounted monitor preferably by pressing the NEXT button 116 on the patient companion assembly 100, as shown. This preferably causes the patient parameters to appear on the wall-mounted monitor having the next strongest signal strength, here designated by reference numeral 120, and preferably simultaneously terminates display of the patient parameters on the monitor 118, also as shown. The operator may then press an OK button 122 to confirm the monitor selection. Alternatively, the operator may leave the buttons of the patient companion assembly 100 untouched and after a predetermined time duration elapses the monitor selection is automatically confirmed.

It is appreciated that if the originally selected wall monitor 118, shown in stage E, is the wall monitor the operator desired to employ, the operator may press the OK button 122 to confirm the monitor selection.

Reference is now made to FIGS. 2A, 2B and 2C, which, taken together, form a simplified block diagram illustration of patient companion assembly 100 useful in the operator controlled medical monitoring system of FIGS. 1A and 1B. As seen in FIGS. 2A-2C, the patient companion assembly comprises a plurality of medical sensor interface subunits. A first medical sensor interface subunit, designated by reference numeral 150, preferably processes inputs from pressure sensors, such as intracranial pressure sensors, arterial pressure sensors and venous pressure sensors. Typically, interface subunit 150 includes five pressure sensor connectors 152, such as connectors 110 (FIGS. 1A and 1B), each adapted to be coupled to a separate pressure sensor and each connected to a pressure input channel interface 154, typically including an amplifier and a filter. The outputs of pressure input channel interfaces 154 are preferably supplied via an A/D converter 156 and a multiplexer 158 to a pressure sensor input processor 160, which adapts the signals for digital wireless communication and supplies them to a digital wireless communications subsystem 162 including a wireless transceiver 164.

Turning to FIG. 2B, it is seen that patient companion assembly 100 additionally includes a second medical sensor interface subunit, designated by reference numeral 170, which preferably processes inputs from a plurality of ECG electrodes. Typically, interface subunit 170 includes a single multi-channel ECG connector 172 having plural channels, each connected to an ECG input channel interface 174, typically including an amplifier and a filter. The output signals from ECG input channel interfaces 174 are preferably supplied via an A/D converter 176 and a multiplexer 178 to an ECG input processor 180, which adapts the signals for digital wireless communication and supplies them to digital wireless communications subsystem 162.

A third medical sensor interface subunit, designated by reference numeral 190, preferably processes inputs from a SPO2 sensor. Typically, interface subunit 190 includes a single SPO2 connector 192 connected to an SPO2 input channel interface 194, typically including an amplifier and a filter. The output signal from SPO2 input channel interface 194 is preferably supplied via an A/D converter 196 to an SPO2 input processor 198, which adapts the signal for digital wireless communication and supplies it to digital wireless communications subsystem 162.

A fourth medical sensor interface subunit, designated by reference numeral 200, preferably processes inputs from a temperature sensor. Typically, interface subunit 200 includes a single temperature connector 202 connected to a temperature input channel interface 204, typically including an amplifier and a filter. The output signal from temperature input channel interface 204 is preferably supplied via an A/D converter 206 to SPO2 input processor 198, which adapts the signal for digital wireless communication and supplies it to digital wireless communications subsystem 162.

As seen in FIG. 2C, patient companion assembly 100 also includes a fifth medical sensor interface subunit, designated by reference numeral 210, which preferably processes inputs from a blood chemistry sensor. Typically, interface subunit 210 includes at least one blood chemistry connector 212, connected to at least one blood chemistry input channel interface 214, typically including an amplifier and a filter. The output signal from each blood chemistry input channel interface 214 is preferably supplied via an A/D converter 216 to a blood chemistry input processor 218, which adapts the signal for digital wireless communication and supplies it to digital wireless communications subsystem 162.

A sixth medical sensor interface subunit, designated by reference numeral 220, preferably processes inputs from a respiratory parameter sensor. Typically, interface subunit 220 includes at least one respiratory parameter connector 222, connected to at least one respiratory parameter input channel interface 224, typically including an amplifier and a filter. The output signal from each respiratory parameter input channel interface 224 is preferably supplied via an A/D converter 226 to a respiratory parameter input processor 228, which adapts the signal for digital wireless communication and supplies it to digital wireless communications subsystem 162.

It is appreciated that any suitable medical sensor may be coupled to a selectable monitor using the patient companion assembly 100 when equipped with a suitable medical sensor interface unit.

A suitable man-machine interface 230, which typically includes NEXT button 116 and OK button 122, governs the operation of a controller 232, which governs operation of the various elements of the patient companion assembly 100.

Reference is now made to FIGS. 3A and 3B, which, taken together, form a simplified block diagram illustration of a monitor interface assembly useful in the operator controlled medical monitoring system of FIGS. 1A and 1B. As seen in FIGS. 3A and 3B, the monitor interface assembly comprises a plurality of monitor interface subunits. A first pressure monitor interface subunit, designated by reference numeral 250, is preferably adapted to be connected to a pressure sensor socket of a conventional monitor, which typically provides low voltage power.

Monitor interface subunit 250 preferably comprises a digital wireless communications subsystem 252, which includes a wireless transceiver 254 which is operative to receive wireless transmissions from wireless transceiver 164 of patient companion assembly 100, to process the received transmissions and to direct them to corresponding monitor interface subunits.

Monitor interface subunit 250 and typically up to four additional pressure monitor interface subunits, here designated by reference numerals 262, 264, 266 and 268, are preferably provided with plug connectors (not shown) each adapted to be coupled to a separate pressure sensor socket of a monitor. Each of monitor interface subunits 250, 262, 264, 266 and 268 typically includes an amplifier, a filter and a D/A converter, which receives, via a processor, those parts of the received transmissions that are directed thereto by digital wireless communications subsystem 252. The outputs of monitor interface subunits 250, 262, 264, 266 and 268 are preferably supplied to corresponding pressure sensor sockets of the monitor in a conventional form which is suitable for conventional operation of the monitor.

It is a particular feature of the present invention that digital wireless communications subsystem 252 is powered by electrical power which is received in part from multiple ones of the pressure sensor sockets of the monitor. It is a further particular feature of the present invention that each of monitor interface subunits 250, 262, 264, 266 and 268 provides power to the various other monitor interface subunits, some of which are connected to sockets of the monitor which do not provide electrical power.

Turning to FIG. 3B, it is seen that the monitor interface assembly additionally includes an ECG monitor interface subunit 270, which is preferably provided with a multi-channel plug connector (not shown) adapted to be coupled to an ECG socket of the monitor. Monitor interface subunit 270 typically includes multiple amplifiers, filters and D/A converters, which receive, via at least one processor, those parts of the received transmissions related to ECG sensing that are directed thereto by digital wireless communications subsystem 252. The outputs of monitor interface subunit 270 are preferably supplied to a corresponding ECG socket of the monitor in a conventional form which is suitable for conventional operation of the monitor.

An SPO2 monitor interface subunit 272 is preferably provided with a plug connector (not shown) adapted to be coupled to an SPO2 sensor socket of the monitor. Monitor interface subunit 272 typically includes an amplifier, a filter and a D/A converter, which receives, via a processor, those parts of the received transmissions related to SPO2 sensing that are directed thereto by digital wireless communications subsystem 252. The output of monitor interface subunit 272 is preferably supplied to a corresponding SPO2 sensor socket of the monitor in a conventional form which is suitable for conventional operation of the monitor.

A temperature monitor interface subunit 274 is preferably provided with a plug connector (not shown) adapted to be coupled to a temperature sensor socket of the monitor. Monitor interface subunit 274 typically includes an amplifier, a filter and a D/A converter, which receives, via a processor, those parts of the received transmissions related to temperature sensing that are directed thereto by digital wireless communications subsystem 252. The output of monitor interface subunit 274 is preferably supplied to a corresponding temperature sensor socket of the monitor in a conventional form which is suitable for conventional operation of the monitor.

A blood chemistry monitor interface subunit 276 is preferably provided with at least one plug connector (not shown) adapted to be coupled to a blood chemistry sensor socket of the monitor. Monitor interface subunit 276 typically includes at least one amplifier, at least one filter and at least one D/A converter, which receive, via a processor, those parts of the received transmissions related to blood chemistry sensing that are directed thereto by digital wireless communications subsystem 252. The output of monitor interface subunit 276 is preferably supplied to a corresponding blood chemistry sensor socket of the monitor in a conventional form which is suitable for conventional operation of the monitor.

A respiratory parameter monitor interface subunit 278 is preferably provided with at least one plug connector (not shown) adapted to be coupled to a respiratory parameter socket of the monitor. Monitor interface subunit 278 typically includes at least one amplifier, at least one filter and at least one D/A converter, which receives, via at least one processor, those parts of the received transmissions related to respiratory parameter sensing that are directed thereto by digital wireless communications subsystem 252. The outputs of monitor interface subunit 278 are preferably supplied to a corresponding respiratory parameter sensor socket of the monitor in a conventional form which is suitable for conventional operation of the monitor.

A suitable man-machine interface 290 governs the operation of a controller 292, which governs operation of the various elements of the monitor interface assembly. It is appreciated that controller 292 may form part of the monitor interface subunit 250.

Figure 4:
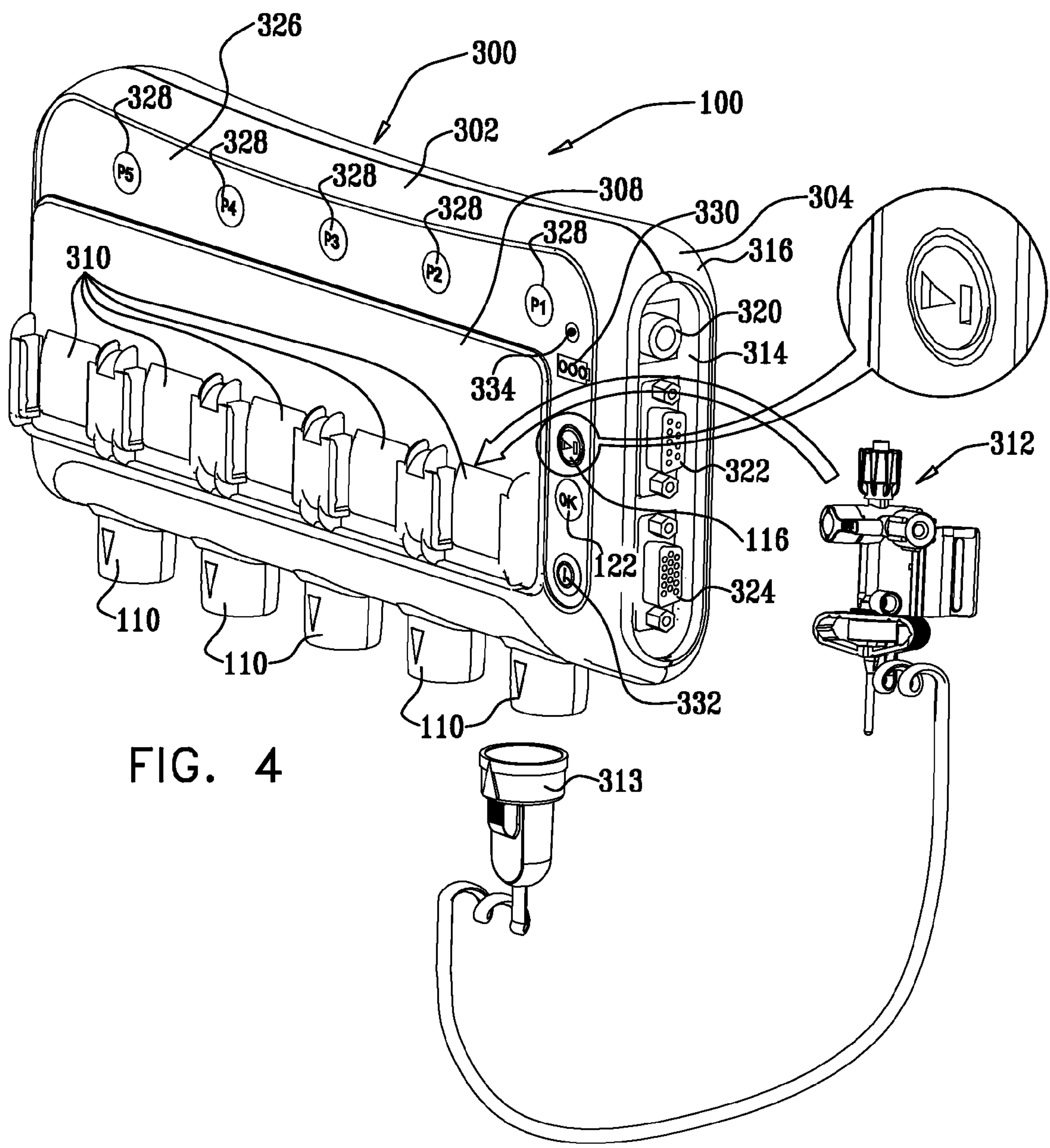
FIG. 4 is a simplified pictorial illustration of the patient companion assembly of FIGS. 1A-2C.

Reference is now made to FIG. 4, which is a simplified pictorial illustration of the patient companion assembly of FIGS. 1A-2C. As seen in FIG. 4, the patient companion assembly 100 comprises a housing 300, preferably composed of a forward portion 302 and a rear portion 304, which preferably encloses the apparatus of FIGS. 2A-2C. Mounted on a bottom edge of housing 300 are a plurality of pressure transducer connector sockets 110, preferably five sockets 110, such as an RJ11 female modular jack, commercially available from Bel-Fuse of Glen Rock, Pa., USA. Each socket 110 preferably includes a suitable pressure sensor connector (not shown) which is coupled to pressure input channel interface 154 (FIGS. 2A-2C). A front panel 308 preferably defines mounting attachment protrusions arranged to define a plurality of pressure transducer mounting sockets 310, preferably five sockets 310, which are adapted to removably support conventional blood pressure transducer assemblies 312, each including a connector 313, such as Transpac IT, commercially available from Elcam Medical A.C.A.L. of Kibbutz Baram, Israel, under catalog designation "fully integrated disposable blood pressure transducer".

Mounted in a recess 314 at a side edge 316 of housing 300 there is preferably provided an SPO2 connector socket 320, such as a D-Type 9S connector socket commercially available from Molex of Illinois, USA, which preferably includes a suitable SPO2 sensor connector (not shown) which is coupled to SPO2 input channel interface 194 (FIGS. 2A-2C). At recess 314 there is additionally provided an ECG sensor socket 322, such as a conventional female D-Type 15S connector socket commercially available from Molex of Illinois, USA, which preferably includes a suitable ECG sensor connector (not shown) which is coupled to ECG input channel interface 174 (FIGS. 2A-2C). Further provided at recess 314 is a temperature sensor socket 324, such as a conventional female RS Phone jack ¼" socket commercially available from Switchcraft Inc. of Chicago, Ill., USA, which preferably includes a suitable temperature sensor connector (not shown) which is coupled to temperature input channel interface 204 (FIGS. 2A-2C).

Located alongside front panel 308 is a control panel 326 including a plurality of pressure channel control buttons 328, preferably five buttons 328, which control operation of the blood pressure transducer assemblies 312. Also preferably included in the control panel 326 is a battery charge status indicator 330, a NEXT button 116, described hereinabove with reference to FIGS. 1A-2C, an OK button 122, described hereinabove with reference to FIGS. 1A-2C, a power on/off button 332 and an audio/visual alarm indicator 334.

Reference is now made to FIG. 5, which is a simplified flow chart illustration of the operation of the system of FIGS. 1A-4. As seen in FIG. 5, when the power on/off button 332 (FIG. 4) is in a power-off state, operation of the patient companion assembly 100 (FIGS. 1A-1B) is initiated either by an operator pressing the power on/off button 332 or by an operator inserting connector 313 of the blood pressure transducer 312 into a socket 110 (FIG. 4). Various system checks are carried out automatically by the controller 232 of FIGS. 2A-2C. If a problem is encountered, an alarm is preferably indicated by audio/visual indicator 334 (FIG. 4) and the patient companion assembly power is shut down.

If no problem is encountered during the system checks, an attempt is made to establish wireless communication with digital wireless communication subsystem 252 (FIGS. 3A and 3B) of a monitor such as monitor 102 (FIGS. 1A-1B). The wireless transceiver 164 of the patient companion assembly 100 (FIGS. 2A-2C) ranks receivers in its vicinity according to the strength of a signal emitted therefrom. Typically, a predetermined number of receivers, preferably 3, are ranked.

Thereafter, an attempt is made by the digital wireless communication subsystem 162 of the patient companion assembly 100 to establish communication with digital wireless communication subsystem 252 of the monitor having the highest ranking. The monitor that is being communicated with indicates the communication thereof by providing an audio/visual indication, such as a triangular waveform, for a predetermined time duration, typically 10 seconds.

If the NEXT button 116 (FIG. 4) is pressed during the predetermined time duration, an attempt is made by the digital wireless communication subsystem 162 of the patient companion assembly 100 to establish communication with digital wireless communication subsystem 252 of the monitor having the next ranking.

If the OK button 122 (FIG. 4) is pressed during the predetermined time duration, or if none of the buttons of control panel 326 (FIG. 4) of the patient companion assembly 100 were pressed during the predetermined time duration, the patient companion assembly confirms the establishing of communication with the selected monitor.

Following confirmation, and if a sensor is connected to a socket of the patient companion assembly 100 the selected monitor displays the sensor signals transmitted by the transmitter 164 of the patient companion assembly 100. If no sensor is connected to a socket of the patient companion assembly, the patient companion assembly continues in an idle state for a predetermined time duration, and if no sensor is connected during that time, the patient companion assembly power is shut down.

Alternatively, the patient companion assembly 100 may attempt establishing communication with one of the monitors only when a sensor is connected to a suitable socket of the patient companion assembly.

Figure 6A:
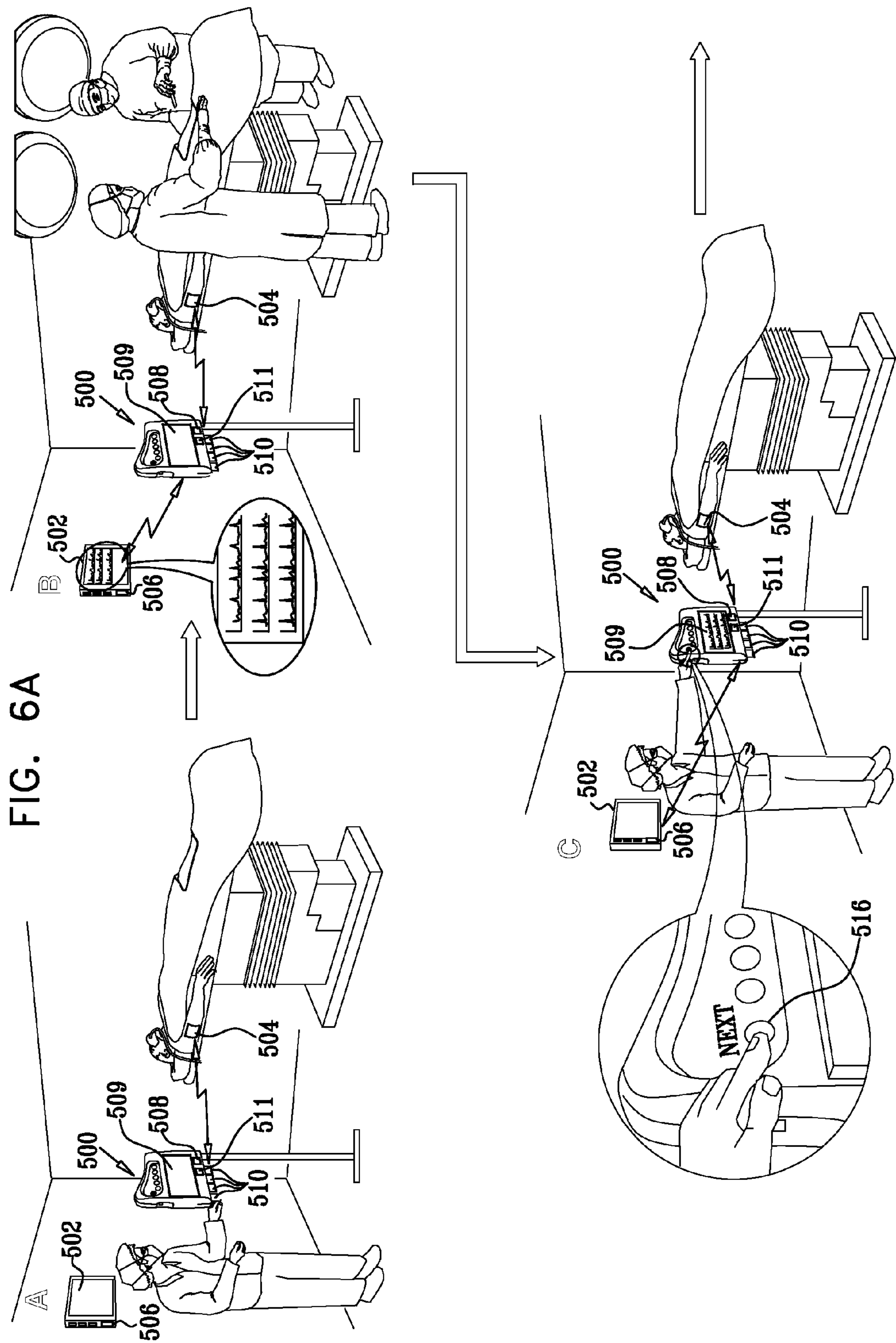
FIGS. 6A and 6B, taken together, are a simplified pictorial illustration of the operation of a operator controlled medical monitoring system constructed and operative in accordance with another preferred embodiment of the present invention FIGS. 7A, 7B and 7C, taken together, form a simplified block diagram illustration of a patient companion assembly useful in the operator controlled medical monitoring system of FIGS. 6A and 6B.
Figure 6B:
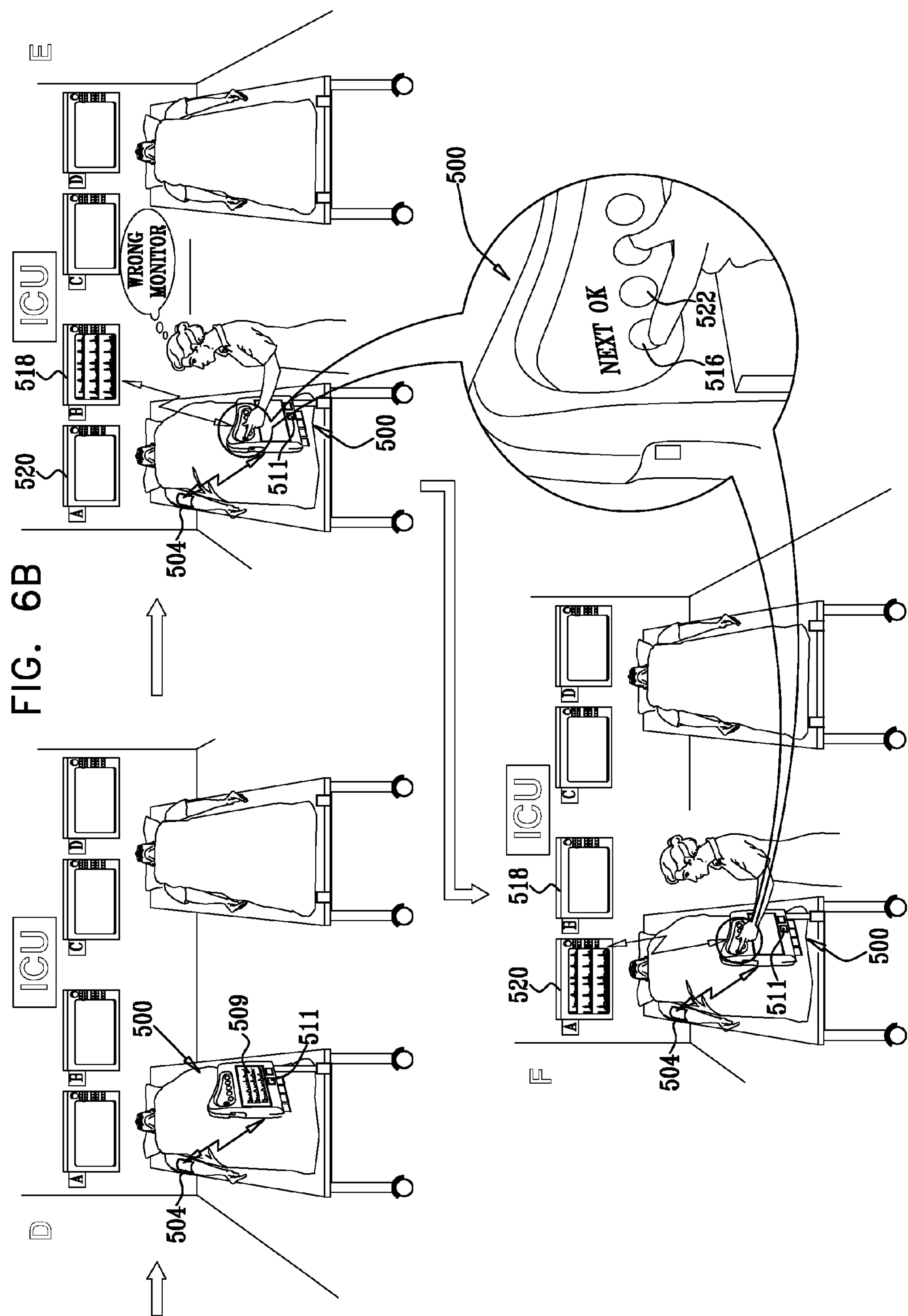

Reference is now made to FIGS. 6A and 6B, which, taken together, are a simplified pictorial illustration of the operation of a operator controlled medical monitoring system constructed and operative in accordance with another preferred embodiment of the present invention. As seen in FIGS. 6A and 6B, there is provided an operator controlled medical monitoring system including a medical sensor that is adapted to monitor a patient characteristic; a plurality of medical monitors, each including a wireless receiver and a medical information output device; and a patient companion assembly, including a medical monitor selector employed by an operator to select one of the plurality of medical monitors and to establish communication between the medical sensor and a selected one of the plurality of medical monitors.

Turning to FIG. 6A, at stage A, there is seen a patient, typically in an operating room environment. In accordance with a preferred embodiment of the present invention, the patient is coupled to a patient companion assembly 500 which includes a medical monitor selector which can be employed by an operator to select one of a plurality of medical monitors, such as a conventional medical monitor 502, and to establish communication between medical sensing devices, such as a blood pressure sensor 504, attached to the patient and the selected medical monitor, preferably via a wireless receiver 506 associated with the medical monitor 502. It is noted that in the embodiment shown in FIG. 6A, a wireless connection is provided between the sensor 504 and the patient companion assembly 500. Preferably, the connection between the patient companion assembly 500 and the medical monitor 502 is wireless and employs a transmitter 508, preferably forming part of the patient companion assembly 500, which communicates with wireless receiver 506. As seen in FIG. 6A, the patient companion assembly 500 additionally includes a monitor 509. It is also appreciated that the medical sensor may be mounted on the patient, as shown in FIG. 6A, or otherwise coupled to the patient. Examples of medical sensor devices that may be coupled to the patient and mounted on the patient companion assembly 500 include physiological pressure sensors.

FIG. 6A shows the sensor 504 transmitting patient information to one or more sensor input receivers 510 of the patient companion assembly 500. Preferably, the patient companion assembly senses changes in the electrical characteristics in the connection circuitry, such as changes of impedance, which are a result of the wireless connection of the medical sensing device. The change in the electrical characteristics is preferably sensed by secondary circuitry 511 formed in the patient companion assembly 500, which is constantly or routinely operational. The wireless connection of the medical sensing device, sensed by circuitry 511, initiates powering up of the patient companion assembly 500.

At stage B, the patient is being operated on in the same location as that shown at stage A. It is seen that monitor 502 is displaying various patient parameters received from medical sensing devices, such as sensor 504, via the patient companion assembly 500, transmitter 508 and receiver 506. As seen at stage B, monitor 509 of patient companion assembly also displays the patient parameters received by sensor input receiver 510.

At stage C, following the operation in Stage B, the patient is being prepared for transfer to another location and the operator is shown terminating communication between the patient companion assembly 500 and the medical monitor 502, typically by pressing a NEXT button 516 on the patient companion assembly 500. This typically results in the patient parameters appearing on the monitor 509, as shown, and preferably simultaneously the patient parameters no longer appear on the monitor 502, also as shown. Moreover, whenever communication between the patient companion assembly 500 and an external medical monitor, such as medical monitor 502, is terminated, the patient parameters are displayed on monitor 509 of the patient companion assembly.

It is appreciated that in any case in which the communication between the patient companion assembly 500 and an external monitor, such as monitor 502, is terminated, the patient parameters are automatically displayed on monitor 509. It is also appreciated that during the time in which the patient companion assembly 500 is in communication with an external monitor, such as monitor 502, the patient parameters are not displayed on monitor 509 in order to conserve energy.

As seen in FIG. 6B, stage D illustrates the patient following his transfer to an ICU or other recovery room, still coupled to patient companion assembly 500 including monitor 509, which continues to display the patient parameters.

At stage E, initial selection of one of a plurality of wall-mounted monitors is shown. The selection is typically carried out by an operator pressing the NEXT button 516 on the patient companion assembly 500. The selection typically enables the patient parameters to appear on the selected wall-mounted monitor, here designated 518, and display of the patient parameters on monitor 509 of patient companion assembly 500, is terminated.

In situations where there are plural wall-mounted monitors available for communication with the patient companion assembly 500, the selection of a wall-mounted monitor preferably is based on the strongest wireless signal sensed by the patient companion assembly 500. In the illustration at stage E, wall-mounted monitor 518 is not the wall-mounted monitor that the operator desires to employ. Accordingly, in accordance with a preferred embodiment of the present invention, and as shown at stage F, the operator can select an alternative wall-mounted monitor preferably by pressing the NEXT button 516 on the patient companion assembly 500, as shown. This preferably causes the patient parameters to appear on the wall-mounted monitor having the next strongest signal strength, here designated by reference numeral 520, and preferably simultaneously terminates display of the patient parameters on the monitor 518, also as shown. The operator may then press an OK button 522 to confirm the monitor selection. Alternatively, the operator may leave the buttons of the patient companion assembly 500 untouched and after a predetermined time duration elapses the monitor selection is automatically confirmed.

Figure 7A:
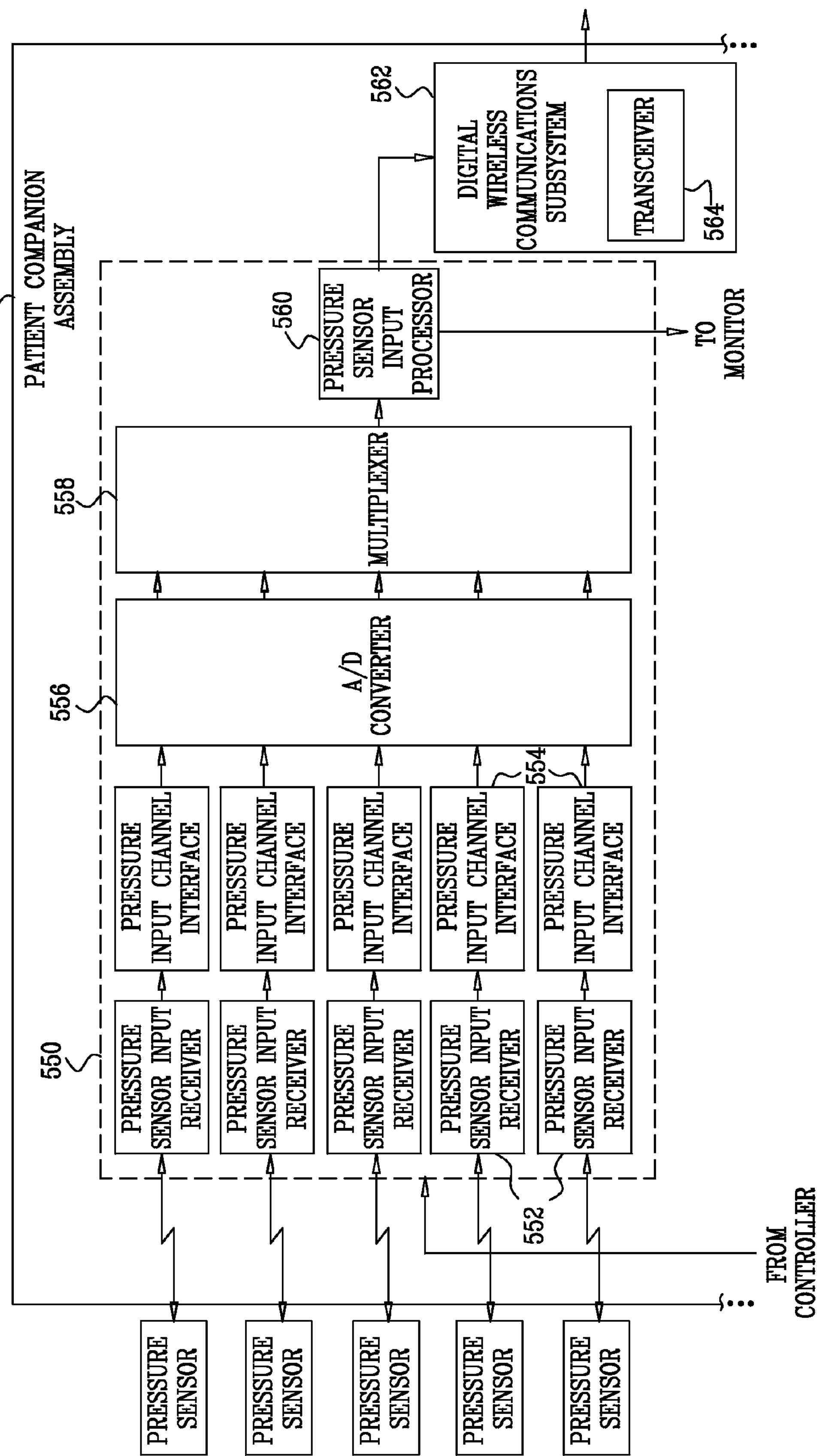

Reference is now made to FIGS. 7A, 7B and 7C, which, taken together, form a simplified block diagram illustration of patient companion assembly 500 useful in the operator controlled medical monitoring system of FIGS. 6A and 6B. As seen in FIGS. 7A-7C, the patient companion assembly 500 comprises a plurality of medical sensor interface subunits. A first medical sensor interface subunit, designated by reference numeral 550, preferably processes inputs from pressure sensors, such as intracranial pressure sensors, arterial pressure sensors and venous pressure sensors. Typically, interface subunit 550 includes five pressure sensor input receivers 552, such as input receivers 510, each adapted to receive input from a separate pressure sensor via a wireless connection, and each connected to a pressure input channel interface 554, typically including an amplifier and a filter. The outputs of pressure input channel interfaces 554 are preferably supplied via an A/D converter 556 and a multiplexer 558 to a pressure sensor input processor 560, which adapts the signals for digital wireless communication and supplies them to a digital wireless communications subsystem 562 including a wireless transceiver 564.

Turning to FIG. 7B, it is seen that patient companion assembly 500 additionally includes a second medical sensor interface subunit, designated by reference numeral 570, which preferably processes inputs from a plurality of ECG electrodes. Typically, interface subunit 570 includes a single multi-channel ECG input receiver 572 having plural channels, each adapted to receive ECG inputs from one ECG electrode via a wireless connection and each connected to an ECG input channel interface 574, typically including an amplifier and a filter. The output signals from ECG input channel interfaces 574 are preferably supplied via an A/D converter 576 and a multiplexer 578 to an ECG input processor 580, which adapts the signals for digital wireless communication and supplies them to digital wireless communications subsystem 562.

A third medical sensor interface subunit, designated by reference numeral 590, preferably processes inputs from a SPO2 sensor. Typically, interface subunit 590 includes a single SPO2 input receiver 592 which is adapted to receive inputs from a SPO2 sensor via a wireless connection and which is connected to an SPO2 input channel interface 594, typically including an amplifier and a filter. The output signal from SPO2 input channel interface 594 is preferably supplied via an A/D converter 596 to an SPO2 input processor 598, which adapts the signal for digital wireless communication and supplies it to digital wireless communications subsystem 562.

A fourth medical sensor interface subunit, designated by reference numeral 600, preferably processes inputs from a temperature sensor. Typically, interface subunit 600 includes a single temperature input receiver 602 which is adapted to receive inputs from a temperature sensor via a wireless connection and which is connected to a temperature input channel interface 604, typically including an amplifier and a filter. The output signal from temperature input channel interface 604 is preferably supplied via an A/D converter 606 to SPO2 input processor 598, which adapts the signal for digital wireless communication and supplies it to digital wireless communications subsystem 562.

As seen in FIG. 7C, patient companion assembly 500 also includes a fifth medical sensor interface subunit, designated by reference numeral 610, which preferably processes inputs from a blood chemistry sensor. Typically, interface subunit 610 includes at least one blood chemistry input receiver 612, which is adapted to receive inputs from at least one blood chemistry sensor via a wireless connection and which is connected to at least one blood chemistry input channel interface 614, typically including an amplifier and a filter. The output signal from each blood chemistry input channel interface 614 is preferably supplied via an A/D converter 616 to a blood chemistry input processor 618, which adapts the signal for digital wireless communication and supplies it to digital wireless communications subsystem 562.

A sixth medical sensor interface subunit, designated by reference numeral 620, preferably processes inputs from a respiratory parameter sensor. Typically, interface subunit 620 includes at least one respiratory parameter input receiver 622, which is adapted to receive inputs from at least one respiratory sensor via a wireless connection and which is connected to at least one respiratory parameter input channel interface 624, typically including an amplifier and a filter. The output signal from each respiratory parameter input channel interface 624 is preferably supplied via an A/D converter 626 to a respiratory parameter input processor 628, which adapts the signal for digital wireless communication and supplies it to digital wireless communications subsystem 562.

It is appreciated that any suitable medical sensor may be coupled to a selectable monitor using the patient companion assembly 500 when equipped with a suitable medical sensor interface unit.

A suitable man-machine interface 630, which typically includes NEXT button 516 and OK button 522, governs the operation of a controller 632, which governs operation of the various elements of the patient companion assembly 500. Controller 632 preferably includes secondary circuitry 511, which senses changes in the electrical characteristics when a sensor wirelessly communicates with the patient companion assembly 500, and thereafter the secondary circuitry powers up the patient companion assembly. Controller 632 additionally controls the display of patient parameters, which are provided by one or more of input processors 560, 580, 598, 618 and 628, on monitor 509.

Figure 8A:
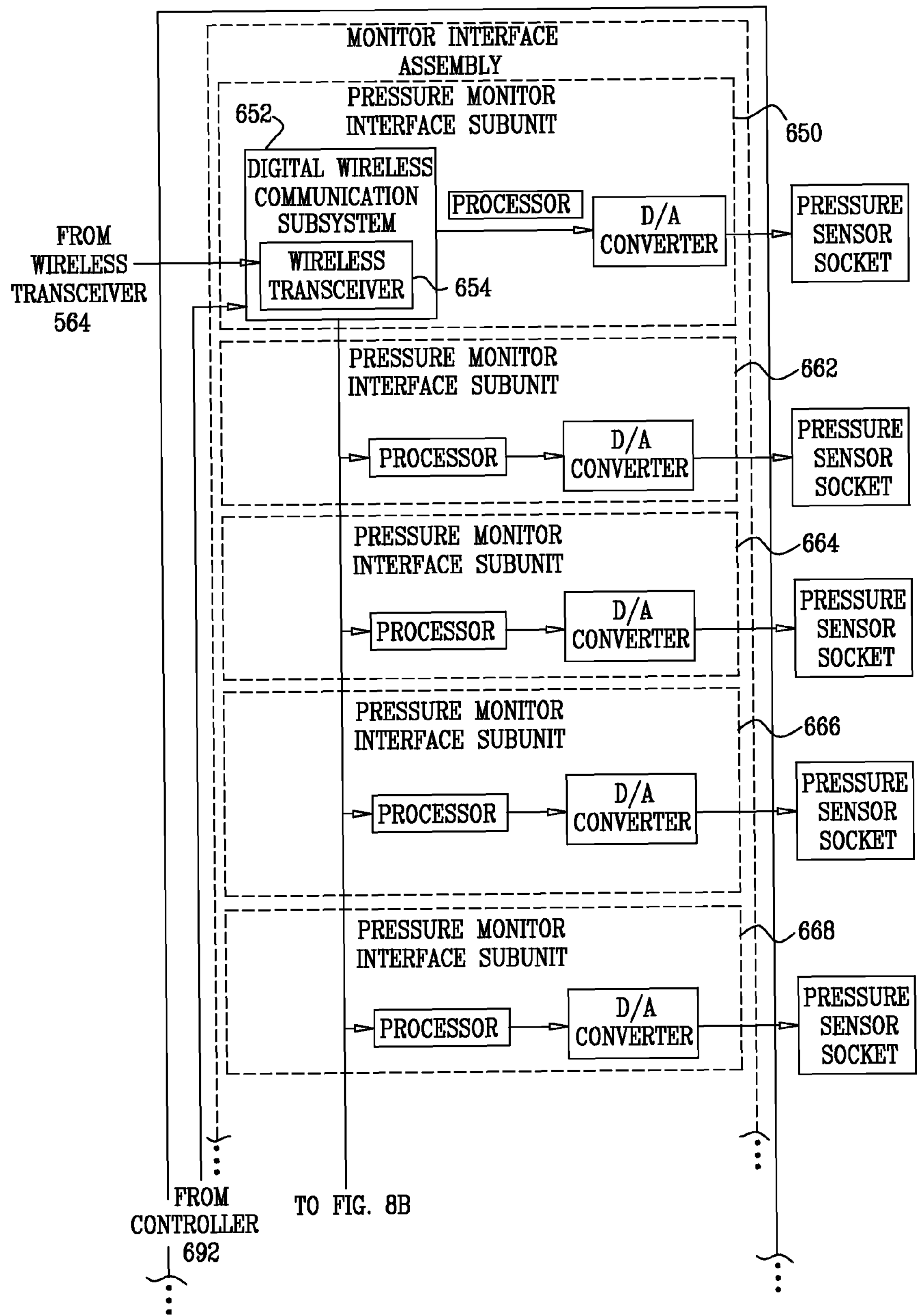
FIGS. 8A and 8B, taken together, form a simplified block diagram illustration of a monitor interface assembly useful in the operator controlled medical monitoring system of FIGS. 6A and 6B.
Figure 8B:
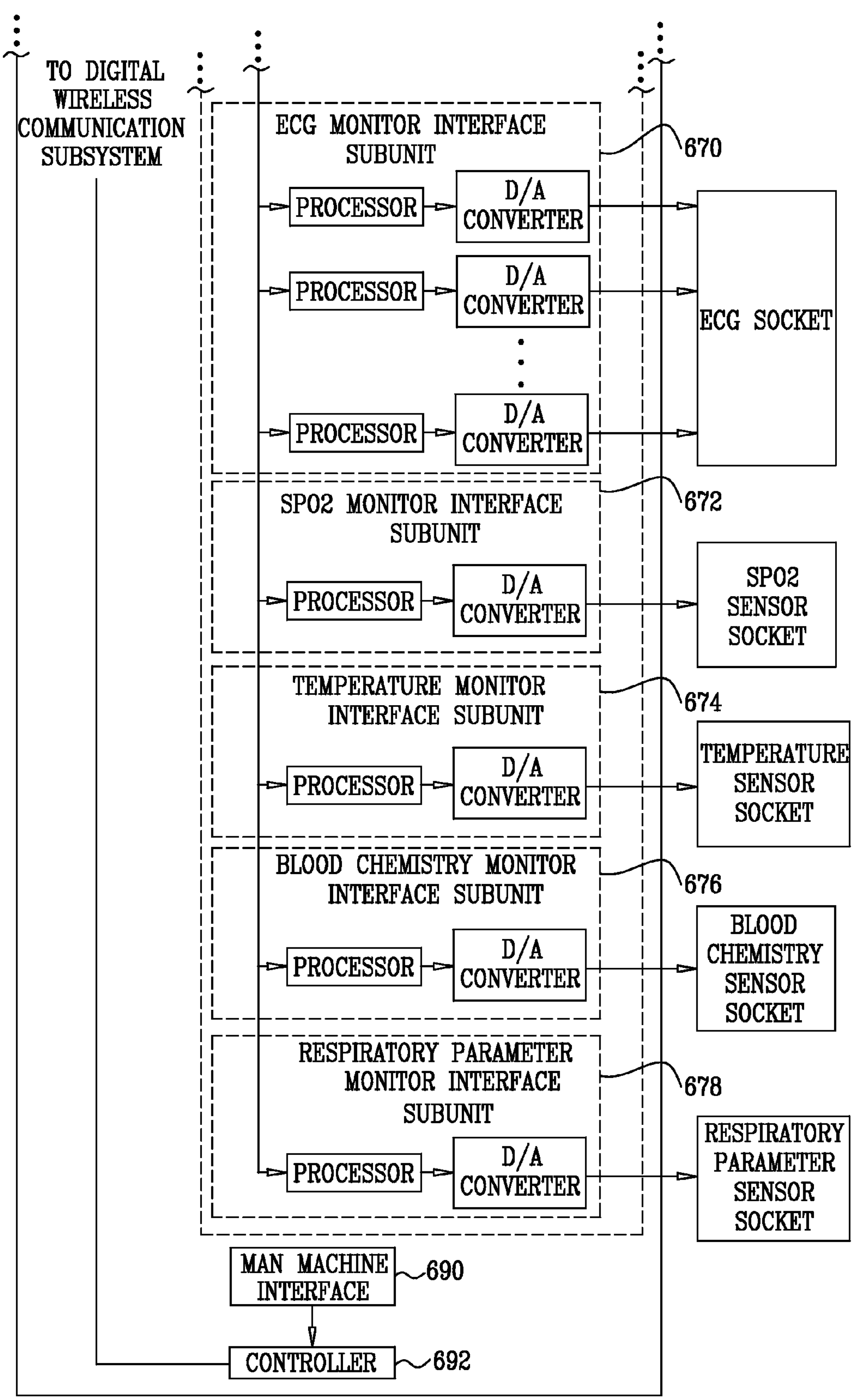

Reference is now made to FIGS. 8A and 8B, which, taken together, form a simplified block diagram illustration of a monitor interface assembly useful in the operator controlled medical monitoring system of FIGS. 6A and 6B. As seen in FIGS. 8A and 8B, the monitor interface assembly comprises a plurality of monitor interface subunits. A first pressure monitor interface subunit, designated by reference numeral 650, is preferably adapted to be connected to a pressure sensor socket of a conventional monitor, which typically provides low voltage power.

Monitor interface subunit 650 preferably comprises a digital wireless communications subsystem 652, which includes a wireless transceiver 654 which is operative to receive wireless transmissions from wireless transceiver 564 of patient companion assembly 500, to process the received transmissions and to direct them to corresponding monitor interface subunits.

Monitor interface subunit 650 and typically up to four additional pressure monitor interface subunits, here designated by reference numerals 662, 664, 666 and 668, are preferably provided with plug connectors (not shown) each adapted to be coupled to a separate pressure sensor socket of a monitor. Each of monitor interface subunits 650, 662, 664, 666 and 668 typically includes an amplifier, a filter and a D/A converter, which receives, via a processor, those parts of the received transmissions that are directed thereto by digital wireless communications subsystem 652. The outputs of monitor interface subunits 650, 662, 664, 666 and 668 are preferably supplied to corresponding pressure sensor sockets of the monitor in a conventional form which is suitable for conventional operation of the monitor.

It is a particular feature of the present invention that digital wireless communications subsystem 652 is powered by electrical power which is received in part from multiple ones of the pressure sensor sockets of the monitor. It is a further particular feature of the present invention that each of monitor interface subunits 650, 662, 664, 666 and 668 provides power to the various other monitor interface subunits, some of which are connected to sockets of the monitor which do not provide electrical power.

Turning to FIG. 8B, it is seen that the monitor interface assembly additionally includes an ECG monitor interface subunit 670, which is preferably provided with a multi-channel plug connector (not shown) adapted to be coupled to an ECG socket of the monitor. Monitor interface subunit 670 typically includes multiple amplifiers, filters and D/A converters, which receive, via at least one processor, those parts of the received transmissions related to ECG sensing that are directed thereto by digital wireless communications subsystem 652. The outputs of monitor interface subunit 670 are preferably supplied to a corresponding ECG socket of the monitor in a conventional form which is suitable for conventional operation of the monitor.

An SPO2 monitor interface subunit 672 is preferably provided with a plug connector (not shown) adapted to be coupled to an SPO2 sensor socket of the monitor. Monitor interface subunit 672 typically includes an amplifier, a filter and a D/A converter, which receives, via a processor, those parts of the received transmissions related to SPO2 sensing that are directed thereto by digital wireless communications subsystem 652. The output of monitor interface subunit 672 is preferably supplied to a corresponding SPO2 sensor socket of the monitor in a conventional form which is suitable for conventional operation of the monitor.

A temperature monitor interface subunit 674 is preferably provided with a plug connector (not shown) adapted to be coupled to a temperature sensor socket of the monitor. Monitor interface subunit 674 typically includes an amplifier, a filter and a D/A converter, which receives, via a processor, those parts of the received transmissions related to temperature sensing that are directed thereto by digital wireless communications subsystem 652. The output of monitor interface subunit 674 is preferably supplied to a corresponding temperature sensor socket of the monitor in a conventional form which is suitable for conventional operation of the monitor.

A blood chemistry monitor interface subunit 676 is preferably provided with at least one plug connector (not shown) adapted to be coupled to a blood chemistry sensor socket of the monitor. Monitor interface subunit 676 typically includes at least one amplifier, at least one filter and at least one D/A converter, which receive, via a processor, those parts of the received transmissions related to blood chemistry sensing that are directed thereto by digital wireless communications subsystem 652. The output of monitor interface subunit 676 is preferably supplied to a corresponding blood chemistry sensor socket of the monitor in a conventional form which is suitable for conventional operation of the monitor.

A respiratory parameter monitor interface subunit 678 is preferably provided with at least one plug connector (not shown) adapted to be coupled to a respiratory parameter socket of the monitor. Monitor interface subunit 678 typically includes at least one amplifier, at least one filter and at least one D/A converter, which receives, via at least one processor, those parts of the received transmissions related to respiratory parameter sensing that are directed thereto by digital wireless communications subsystem 652. The outputs of monitor interface subunit 678 are preferably supplied to a corresponding respiratory parameter sensor socket of the monitor in a conventional form which is suitable for conventional operation of the monitor.

A suitable man-machine interface 690 governs the operation of a controller 692, which governs operation of the various elements of the monitor interface assembly. It is appreciated that controller 692 may form part of the monitor interface subunit 650.

Figure 9:
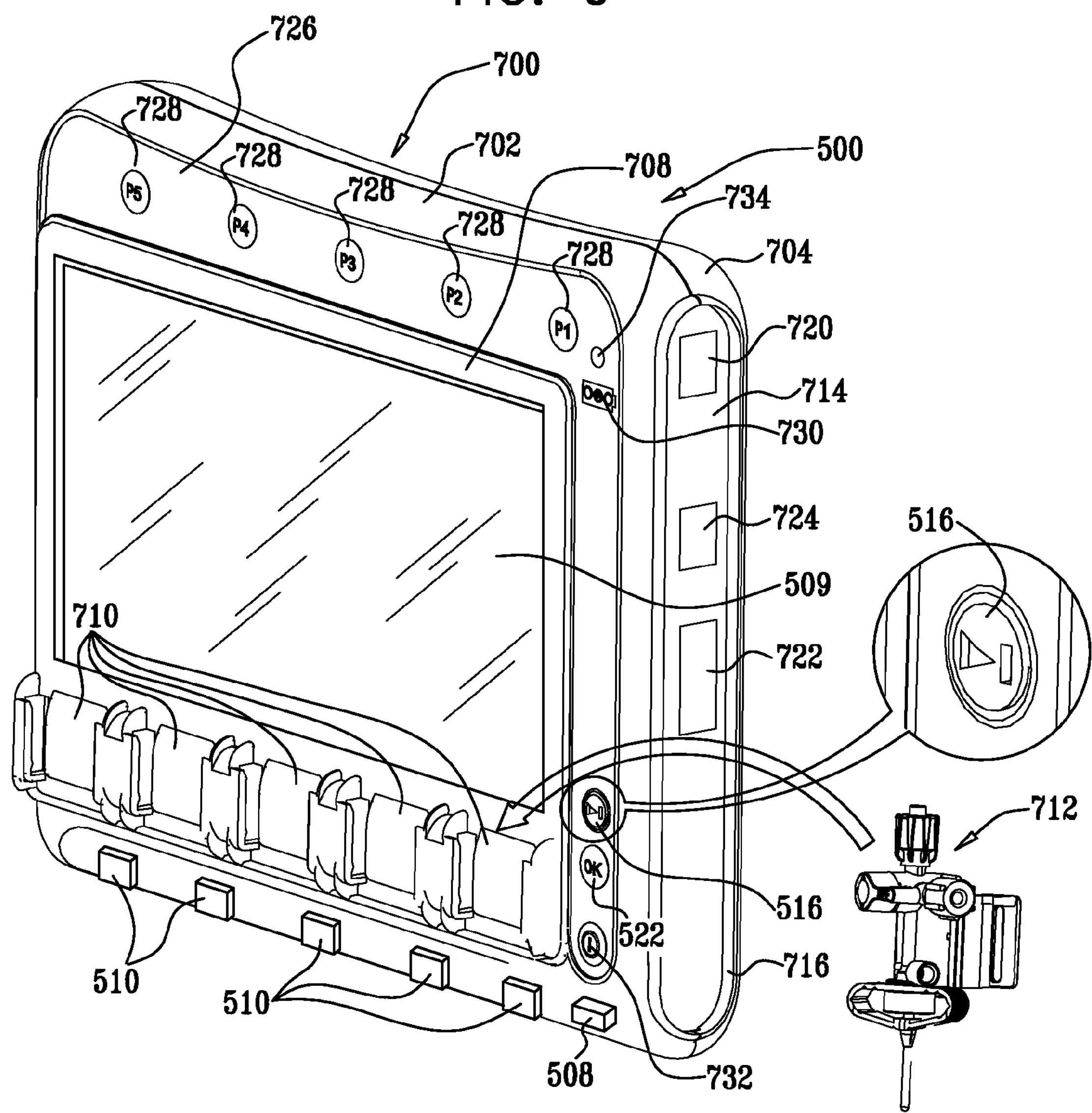
FIG. 9 is a simplified pictorial illustration of the patient companion assembly of FIGS. 6A-7C.

Reference is now made to FIG. 9, which is a simplified pictorial illustration of the patient companion assembly of FIGS. 6A-7C. As seen in FIG. 9, the patient companion assembly 500 comprises a housing 700, preferably composed of a forward portion 702 and a rear portion 704, which preferably encloses the apparatus of FIGS. 7A-7C. Mounted on a bottom edge of housing 700 are a plurality of blood pressure sensor input receivers 510, preferably five input receivers 510. Each input receiver 510 is preferably coupled to pressure input channel interface 554 (FIGS. 7A-7C).

A front panel 708 preferably defines mounting attachment protrusions arranged to define a plurality of pressure transducer mounting sockets 710, preferably five sockets 710, which are adapted to removably support conventional blood pressure transducer assemblies 712, such as Transpac IT, commercially available from Elcam Medical A.C.A.L. of Kibbutz Baram, Israel, under catalog designation "fully integrated disposable blood pressure transducer". Also included in front panel 708 is medical monitor 509, described hereinabove with reference to FIGS. 6A-7C.

Mounted in a recess 714 at a side edge 716 of housing 700 there is preferably provided an SPO2 sensor input receiver 720, which preferably is coupled to SPO2 input channel interface 594 (FIGS. 7A-7C). At recess 714 there is additionally provided an ECG sensor input receiver 722, which preferably is coupled to ECG input channel interface 574 (FIGS. 7A-7C). Further provided at recess 714 is a temperature sensor input receiver 724, which preferably is coupled to temperature input channel interface 604 (FIGS. 7A-7C).

Located alongside front panel 708 is a control panel 726 including a plurality of pressure channel control buttons 728, preferably five buttons 728, which control operation of the blood pressure transducer assemblies 712. Also preferably included in the control panel 726 is a battery charge status indicator 730, a NEXT button 516, described hereinabove with reference to FIGS. 6A-7C, an OK button 522, described hereinabove with reference to FIGS. 6A-7C, a power on/off button 732 and an audio/visual alarm indicator 734.

Reference is now made to FIG. 10, which is a simplified flow chart illustration of the operation of the system of FIGS. 6A-9. As seen in FIG. 10, when the power on/off button 732 (FIG. 9) is in a power-off state, operation of the patient companion assembly 500 (FIGS. 6A-6B) is initiated either by an operator pressing the power on/off button 732 or by receipt of an output signal from a blood pressure transducer 312 by blood pressure sensor input receiver 510 (FIG. 9). Various system checks are carried out automatically by the controller 632 of FIGS. 7A-7C. If a problem is encountered, an alarm is preferably indicated by audio/visual indicator 734 (FIG. 9) and the patient companion assembly power is shut down.

If no problem is encountered during the system checks, an attempt is made to establish wireless communication with digital wireless communication subsystem 652 (FIGS. 8A and 8B) of a monitor such as monitor 502 (FIGS. 6A-6B). The wireless transceiver 564 of the patient companion assembly 500 (FIGS. 7A-7C) ranks receivers in its vicinity according to the strength of a signal emitted therefrom. Typically, a predetermined number of receivers, preferably 3, are ranked.

Thereafter, an attempt is made by the digital wireless communication subsystem 562 of the patient companion assembly 500 to establish communication with digital wireless communication subsystem 652 of the monitor having the highest ranking. The monitor that is being communicated indicates the communication thereof by providing an audio/visual indication, such as a triangular waveform, for a predetermined time duration, typically 10 seconds.

If the NEXT button 516 (FIG. 9) is pressed during the predetermined time duration, an attempt is made by the digital wireless communication subsystem 562 of the patient companion assembly 500 to establish communication with digital wireless communication subsystem 652 of the monitor having the next ranking.

If the OK button 522 (FIG. 9) is pressed during the predetermined time duration, or if none of the buttons of control panel 726 (FIG. 9) of the patient companion assembly 500 were pressed during the predetermined time duration, the patient companion assembly confirms the establishing of communication with the selected monitor.

Following confirmation, and if a signal is received from a sensor by a sensor input receiver of patient companion assembly 500, the selected monitor displays the sensor signals transmitted by the transmitter 564 of the patient companion assembly 500.

If no signal is received from a sensor by a sensor input receiver, such as sensor input receivers 510, the patient companion assembly continues in an idle state for a predetermined amount of time and if no signal is received during that time, the patient companion assembly power is shut down.

Alternatively, the patient companion assembly 100 may attempt establishing communication with one of the monitors only when a sensor is connected to a suitable socket of the patient companion assembly.

It is appreciated that the patient companion assembly may initially establish communication with monitor 509 thereof, prior to attempting establishing communication with other monitors. Additionally, the sensor signal is preferably displayed only on a single monitor at any given time. Therefore, when a monitor other than monitor 509 is selected and the sensor signal is displayed on the selected monitor, the sensor signal is no longer displayed on monitor 509. Similarly, when the display of the sensor signal on an external monitor, such as monitor 502, is terminated, the signal may automatically be displayed on monitor 509.

Figure 11A:
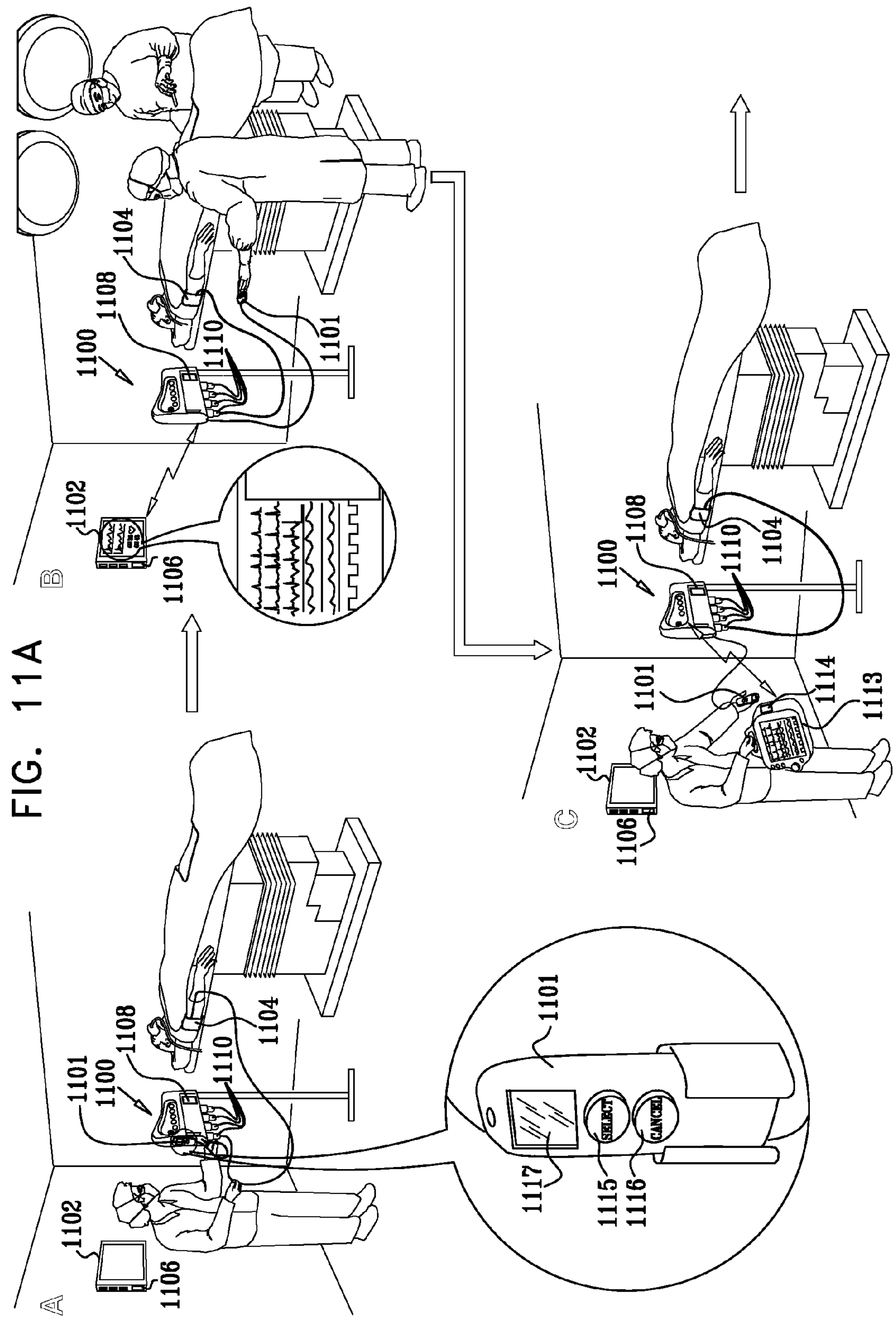
FIGS. 11A and 11B, taken together, are a simplified pictorial illustration of the operation of a operator controlled medical monitoring system constructed and operative in accordance with yet another preferred embodiment of the present invention.
Figure 11B:
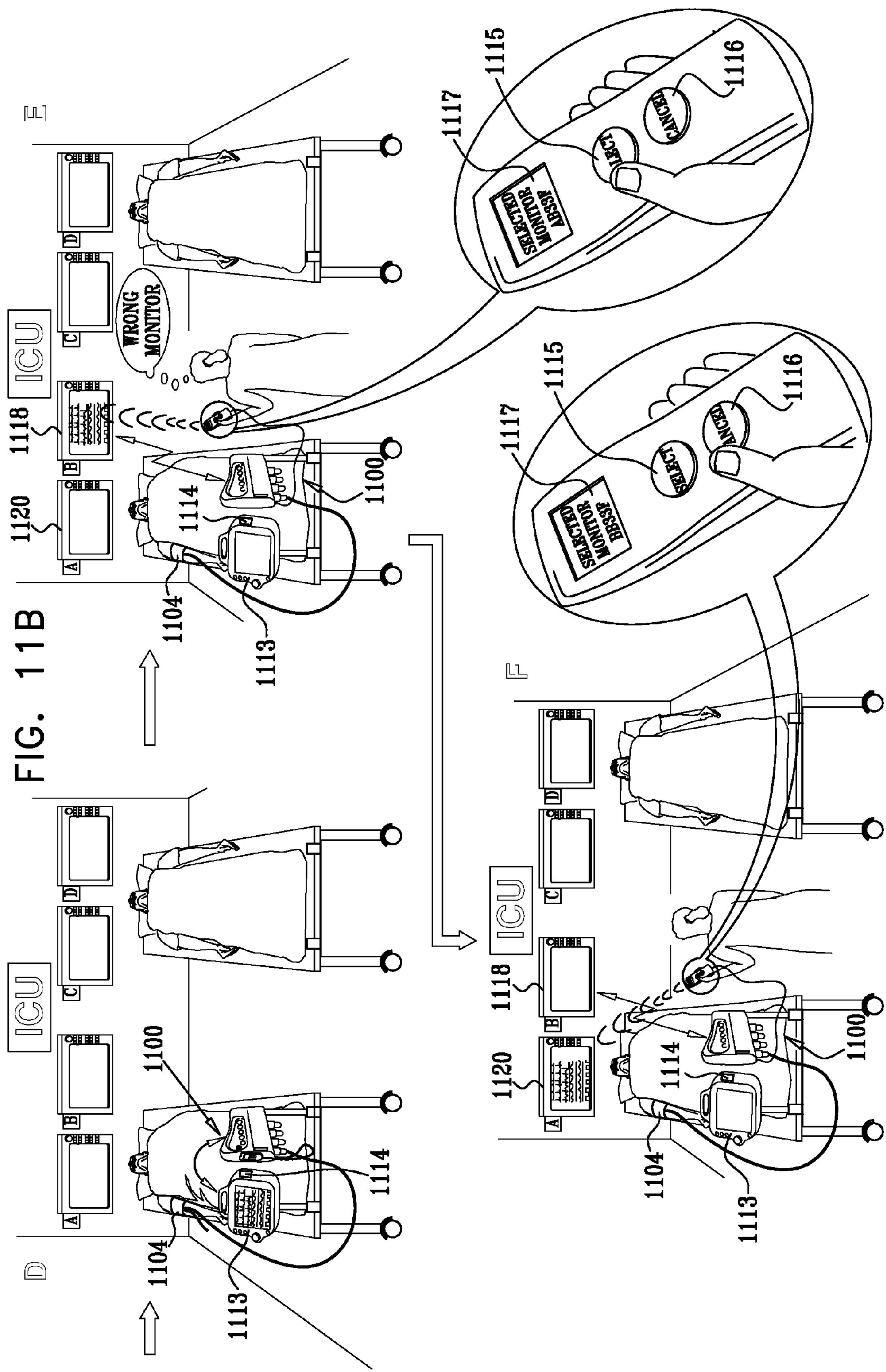

Reference is now made to FIGS. 11A and 11B, which, taken together, are a simplified pictorial illustration of the operation of a operator controlled medical monitoring system constructed and operative in accordance with yet another preferred embodiment of the present invention. As seen in FIGS. 11A and 11B, there is provided an operator controlled medical monitoring system including a medical sensor that is adapted to monitor a patient characteristic; a plurality of medical monitors, each including a wireless receiver and a medical information output device; and a patient companion assembly, including a medical monitor selector employed by an operator to select one of the plurality of medical monitors and to establish communication between the medical sensor and a selected one of the plurality of medical monitors.

Turning to FIG. 11A, at stage A, there is seen a patient, typically in an operating room environment. In accordance with a preferred embodiment of the present invention, the patient is coupled to a patient companion assembly 1100 which includes a medical monitor selector 1101 which can be employed by an operator to select one of a plurality of medical monitors, such as a conventional medical monitor 1102, and to establish communication between medical sensing devices, such as a blood pressure sensor 1104, attached to the patient and the selected medical monitor, preferably via a wireless receiver 1106 associated with the medical monitor 1102. It is noted that in the embodiment shown in FIG. 11A, a wired connection is provided between the sensor 1104 and the patient companion assembly 1100, it being appreciated that alternatively a wireless connection may be provided. Preferably, the connection between the patient companion assembly 1100 and the medical monitor 1102 is wireless and employs a transmitter 1108, preferably forming part of the patient companion assembly 1100, which communicates with wireless receiver 1106.

It is also appreciated that the medical sensor may be mounted on the patient, as shown in FIG. 1A, or otherwise coupled to the patient. Examples of medical sensor devices that may be coupled to the patient and mounted on the patient companion assembly 1100 include physiological pressure sensors. FIG. 11A shows the operator in the process of connecting the sensor 1104 to one of a plurality of connection sockets 1110 of the patient companion assembly 1100. Preferably, connection of a medical sensing device initiates powering up of the patient companion assembly 1100.

At stage B, the patient is being operated on in the same location as that shown at stage A. It is seen that monitor 1102 is displaying various patient parameters received from medical sensing devices, such as sensor 1104, via the patient companion assembly 1100, transmitter 1108 and receiver 1106.

At stage C, following the operation in Stage B, the patient is being prepared for transfer to another location and a conventional portable monitor 1113, preferably having associated therewith a wireless receiver 1114, is introduced. The operator is shown initializing communication between the patient companion assembly 1100 and the portable monitor 1113, typically by directing the monitor selector 1101 toward the portable monitor 1113 and pressing a SELECT button 1115 on the monitor selector 1101 of patient companion assembly 1100. The initializing typically enables the patient parameters to appear on the portable monitor 1113, as shown, and preferably simultaneously terminates display of the patient parameters on the monitor 1102, also as shown. Alternatively, the operator may terminate the display of the patient parameters on the monitor 1102 by directing the monitor selector thereto and pressing a CANCEL button 1116 on the monitor selector 1101. An identification of the selected, active monitor is provided on a display 1117 of monitor selector 1101.

As seen in FIG. 11B, stage D illustrates the patient following his transfer to an ICU or other recovery room, still coupled to portable monitor 1113, which continues to display the patient parameters.

At stage E, initial selection of one of a plurality of wall-mounted monitors is shown. The selection is typically carried out by an operator directing the monitor selector 1101 toward a selected monitor and pressing the SELECT button 1115 on the monitor selector 1101 of the patient companion assembly 1100. The selection typically enables the patient parameters to appear on the selected wall-mounted monitor, here designated 1118, and preferably simultaneously terminates display of the patient parameters on the portable monitor 1113, also as shown. Alternatively, the operator may terminate the display of the patient parameters on the monitor 1113 by directing the monitor selector thereto and pressing CANCEL button 1116 on the monitor selector 1101. An identification of the selected, active monitor is provided on display 1117 of monitor selector 1101.

In situations where there are plural wall-mounted monitors available for communication with the patient companion assembly 1100, the selection of a wall-mounted monitor preferably is based on the direction at which the monitor selector 1101 is pointed during the selection.

In the illustration at stage E, wall-mounted monitor 1118 is not the wall-mounted monitor that the operator desires to employ. Accordingly, in accordance with a preferred embodiment of the present invention, and as shown at stage F, the operator can select an alternative wall-mounted monitor preferably by directing the monitor selector 1101 toward the correct monitor and pressing the SELECT button 1115 on the monitor selector 1101 of patient companion assembly 1100, as shown. This preferably causes the patient parameters to appear on the wall-mounted monitor toward which the monitor selector 1101 was directed, here designated by reference numeral 1120, and preferably simultaneously terminates display of the patient parameters on the monitor 1118, also as shown. Alternatively, the operator may terminate the display of the patient parameters on the monitor 1118 by directing the monitor selector thereto and pressing CANCEL button 1116 on the monitor selector 1101. An identification of the selected, active monitor is provided on display 1117 of monitor selector 1101.

Reference is now made to FIGS. 12A, 12B and 12C, which, taken together, form a simplified block diagram illustration of patient companion assembly 1100 useful in the operator controlled medical monitoring system of FIGS. 11A and 11B. As seen in FIGS. 12A-12C, the patient companion assembly comprises a plurality of medical sensor interface subunits. A first medical sensor interface subunit, designated by reference numeral 1150, preferably processes inputs from pressure sensors, such as intracranial pressure sensors, arterial pressure sensors and venous pressure sensors. Typically, interface subunit 1150 includes five pressure sensor connectors 1152, such as connectors 1110, each adapted to be coupled to a separate pressure sensor and each connected to a pressure input channel interface 1154, typically including an amplifier and a filter. The outputs of pressure input channel interfaces 1154 are preferably supplied via an A/D converter 1156 and a multiplexer 1158 to a pressure sensor input processor 1160, which adapts the signals for digital wireless communication and supplies them to a digital wireless communications subsystem 1162 including a wireless transceiver 1164.

Turning to FIG. 12B, it is seen that patient companion assembly 1100 additionally includes a second medical sensor interface subunit, designated by reference numeral 1170, which preferably processes inputs from a plurality of ECG electrodes. Typically, interface subunit 1170 includes a single multi-channel ECG connector 1172 having plural channels, each connected to an ECG input channel interface 1174, typically including an amplifier and a filter. The output signals from ECG input channel interfaces 1174 are preferably supplied via an A/D converter 1176 and a multiplexer 1178 to an ECG input processor 1180, which adapts the signals for digital wireless communication and supplies them to digital wireless communications subsystem 1162.

A third medical sensor interface subunit, designated by reference numeral 1190, preferably processes inputs from a SPO2 sensor. Typically, interface subunit 1190 includes a single SPO2 connector 1192 connected to an SPO2 input channel interface 1194, typically including an amplifier and a filter. The output signal from SPO2 input channel interface 1194 is preferably supplied via an A/D converter 1196 to an SPO2 input processor 1198, which adapts the signal for digital wireless communication and supplies it to digital wireless communications subsystem 1162.

A fourth medical sensor interface subunit, designated by reference numeral 1200, preferably processes inputs from a temperature sensor. Typically, interface subunit 1200 includes a single temperature connector 1202 connected to a temperature input channel interface 1204, typically including an amplifier and a filter. The output signal from temperature input channel interface 1204 is preferably supplied via an A/D converter 1206 to SPO2 input processor 1198, which adapts the signal for digital wireless communication and supplies it to digital wireless communications subsystem 1162.

As seen in FIG. 12C, patient companion assembly 1100 also includes a fifth medical sensor interface subunit, designated by reference numeral 1210, which preferably processes inputs from a blood chemistry sensor. Typically, interface subunit 1210 includes at least one blood chemistry connector

1212, connected to at least one blood chemistry input channel interface 1214, typically including an amplifier and a filter. The output signal from each blood chemistry input channel interface 1214 is preferably supplied via an A/D converter 1216 to a blood chemistry input processor 1218, which adapts the signal for digital wireless communication and supplies it to digital wireless communications subsystem 1162.

A sixth medical sensor interface subunit, designated by reference numeral 1220, preferably processes inputs from a respiratory parameter sensor. Typically, interface subunit 1220 includes at least one respiratory parameter connector 1222, connected to at least one respiratory parameter input channel interface 1224, typically including an amplifier and a filter. The output signal from each respiratory parameter input channel interface 1224 is preferably supplied via an A/D converter 1226 to a respiratory parameter input processor 1228, which adapts the signal for digital wireless communication and supplies it to digital wireless communications subsystem 1162.

It is appreciated that any suitable medical sensor may be coupled to a selectable monitor using the patient companion assembly 1100 when equipped with a suitable medical sensor interface unit.

A suitable man-machine interface 1230, which typically includes the monitor selector 1101 which includes SELECT button 1115, display 1117 and CANCEL button 1116, governs the operation of a controller 1232, which governs operation of the various elements of the patient companion assembly 1100.

Figure 13A:
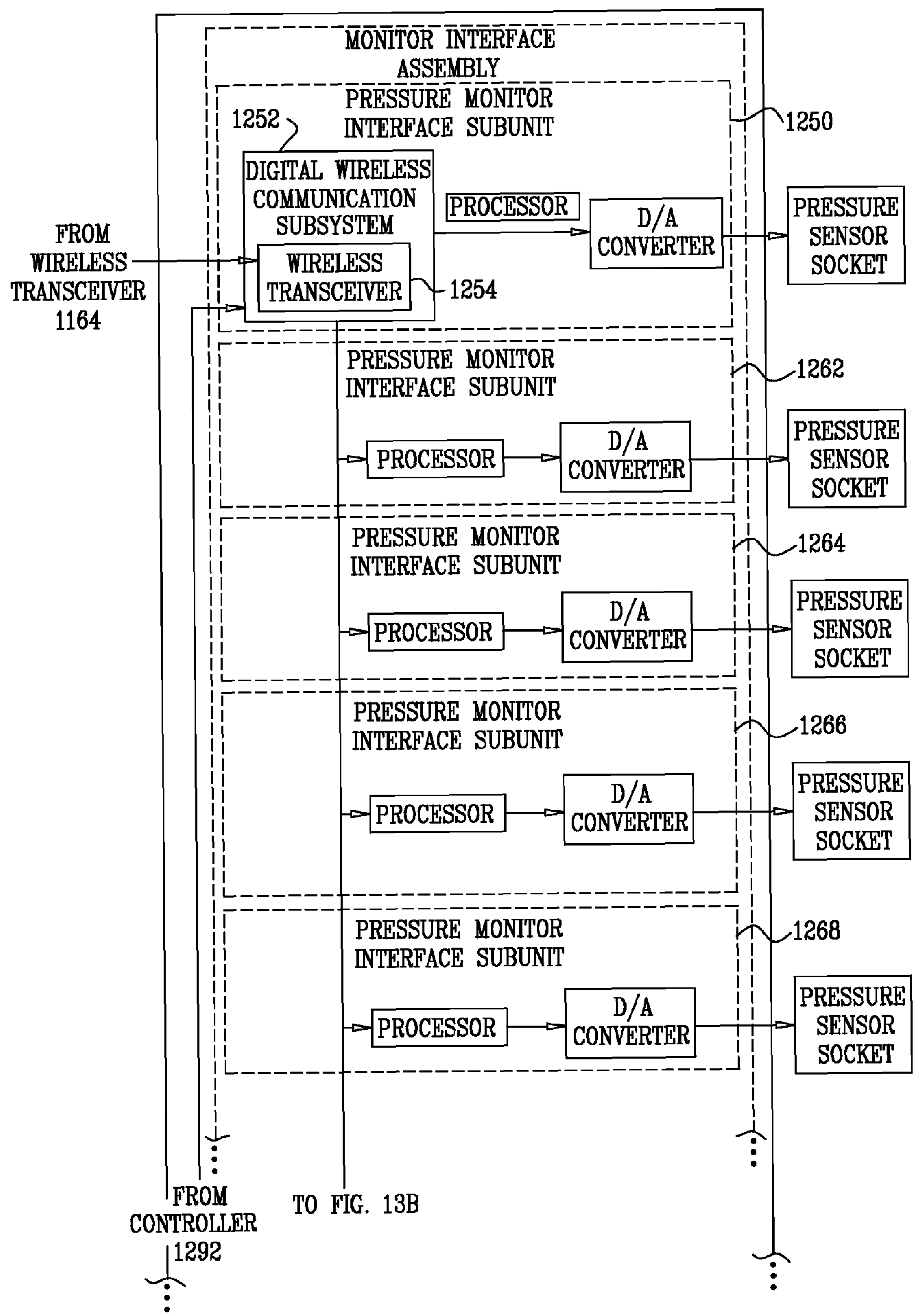
FIGS. 13A and 13B, taken together, form a simplified block diagram illustration of a monitor interface assembly useful in the operator controlled medical monitoring system of FIGS. 11A and 11B.
Figure 13B:
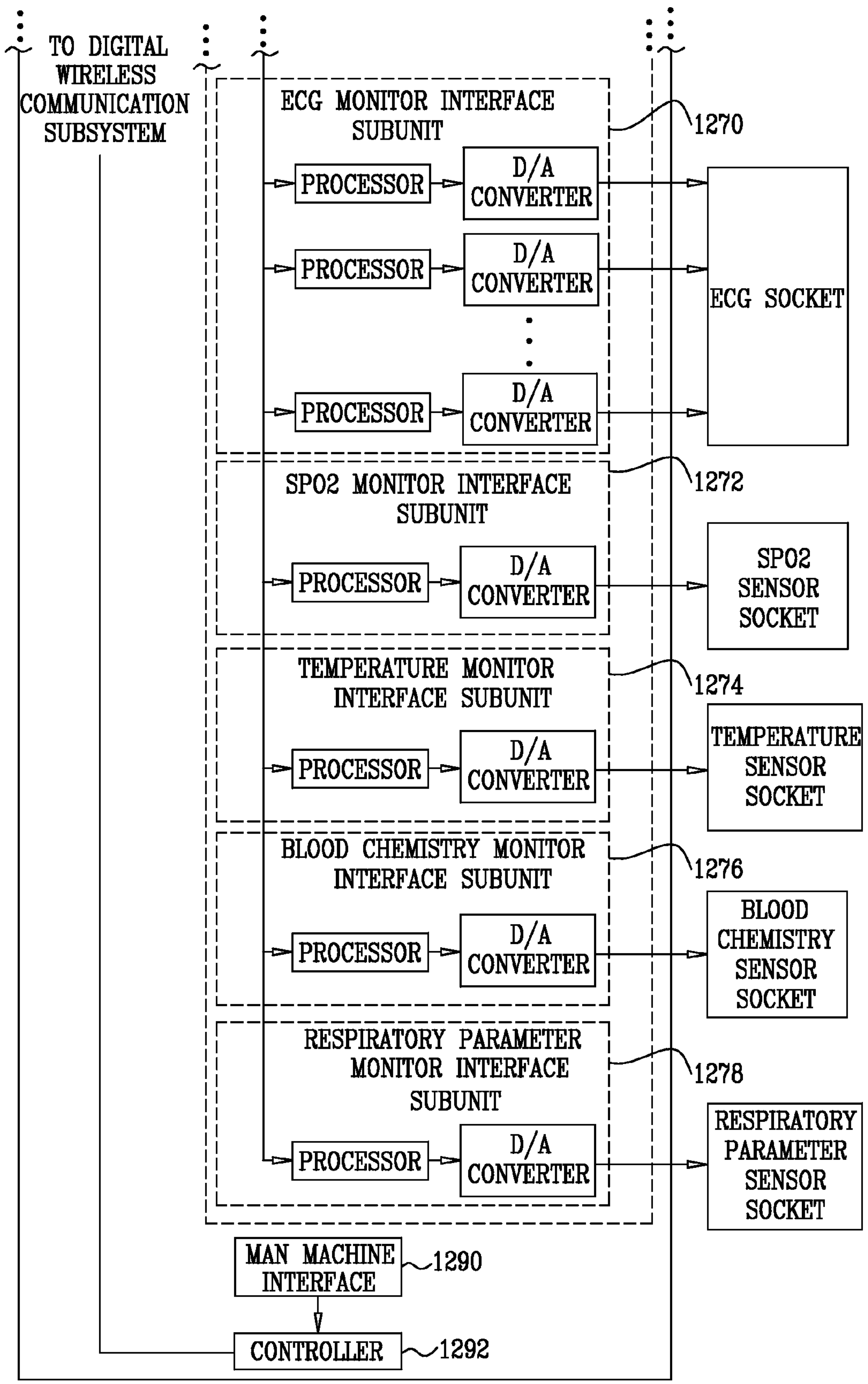

Reference is now made to FIGS. 13A and 13B, which, taken together, form a simplified block diagram illustration of a monitor interface assembly useful in the operator controlled medical monitoring system of FIGS. 11A and 11B. As seen in FIGS. 13A and 13B, the monitor interface assembly comprises a plurality of monitor interface subunits. A first pressure monitor interface subunit, designated by reference numeral 1250, is preferably adapted to be connected to a pressure sensor socket of a conventional monitor, which typically provides low voltage power.

Monitor interface subunit 1250 preferably comprises a digital wireless communications subsystem 1252, which includes a wireless transceiver 1254 which is operative to receive wireless transmissions from wireless transceiver 1164 of patient companion assembly 1100, to process the received transmissions and to direct them to corresponding monitor interface subunits.

Monitor interface subunit 1250 and typically up to four additional pressure monitor interface subunits, here designated by reference numerals 1262, 1264, 1266 and 1268, are preferably provided with plug connectors (not shown) each adapted to be coupled to a separate pressure sensor socket of a monitor. Each of monitor interface subunits 1250, 1262, 1264, 1266 and 1268 typically includes an amplifier, a filter and a D/A converter, which receives, via a processor, those parts of the received transmissions that are directed thereto by digital wireless communications subsystem 1252. The outputs of monitor interface subunits 1250, 1262, 1264, 1266 and 1268 are preferably supplied to corresponding pressure sensor sockets of the monitor in a conventional form which is suitable for conventional operation of the monitor.

It is a particular feature of the present invention that digital wireless communications subsystem 1252 is powered by electrical power which is received in part from multiple ones of the pressure sensor sockets of the monitor. It is a further particular feature of the present invention that monitor interface subunits 1250, 1262, 1264, 1266 and 1268 each provides power to the various other monitor interface subunits, some of which are connected to sockets of the monitor which do not provide electrical power.

Turning to FIG. 13B, it is seen that the monitor interface assembly additionally includes an ECG monitor interface subunit 1270, which is preferably provided with a multichannel plug connector (not shown) adapted to be coupled to an ECG socket of the monitor. Monitor interface subunit 1270 typically includes multiple amplifiers, filters and D/A converters, which receive, via at least one processor, those parts of the received transmissions related to ECG sensing that are directed thereto by digital wireless communications subsystem 1252. The outputs of monitor interface subunit 1270 are preferably supplied to a corresponding ECG socket of the monitor in a conventional form which is suitable for conventional operation of the monitor.

An SPO2 monitor interface subunit 1272 is preferably provided with a plug connector (not shown) adapted to be coupled to an SPO2 sensor socket of the monitor. Monitor interface subunit 1272 typically includes an amplifier, a filter and a D/A converter, which receives, via a processor, those parts of the received transmissions related to SPO2 sensing that are directed thereto by digital wireless communications subsystem 1252. The output of monitor interface subunit 1272 is preferably supplied to a corresponding SPO2 sensor socket of the monitor in a conventional form which is suitable for conventional operation of the monitor.

A temperature monitor interface subunit 1274 is preferably provided with a plug connector (not shown) adapted to be coupled to a temperature sensor socket of the monitor. Monitor interface subunit 1274 typically includes an amplifier, a filter and a D/A converter, which receives, via a processor, those parts of the received transmissions related to temperature sensing that are directed thereto by digital wireless communications subsystem 1252. The output of monitor interface subunit 1274 is preferably supplied to a corresponding temperature sensor socket of the monitor in a conventional form which is suitable for conventional operation of the monitor.

A blood chemistry monitor interface subunit 1276 is preferably provided with at least one plug connector (not shown) adapted to be coupled to a blood chemistry sensor socket of the monitor. Monitor interface subunit 1276 typically includes at least one amplifier, at least one filter and at least one D/A converter, which receive, via a processor, those parts of the received transmissions related to blood chemistry sensing that are directed thereto by digital wireless communications subsystem 1252. The output of monitor interface subunit 1276 is preferably supplied to a corresponding blood chemistry sensor socket of the monitor in a conventional form which is suitable for conventional operation of the monitor.

A respiratory parameter monitor interface subunit 1278 is preferably provided with at least one plug connector (not shown) adapted to be coupled to a respiratory parameter socket of the monitor. Monitor interface subunit 1278 typically includes at least one amplifier, at least one filter and at least one D/A converter, which receives, via at least one processor, those parts of the received transmissions related to respiratory parameter sensing that are directed thereto by digital wireless communications subsystem 1252. The outputs of monitor interface subunit 1278 are preferably supplied to a corresponding respiratory parameter sensor socket of the monitor in a conventional form which is suitable for conventional operation of the monitor.

A suitable man-machine interface 1290 governs the operation of a controller 1292, which governs operation of the various elements of the monitor interface assembly, and which is operative to receive communications commands from monitor selector 1101. It is appreciated that controller 1292 may form part of the monitor interface subunit 1250.

Figure 14:
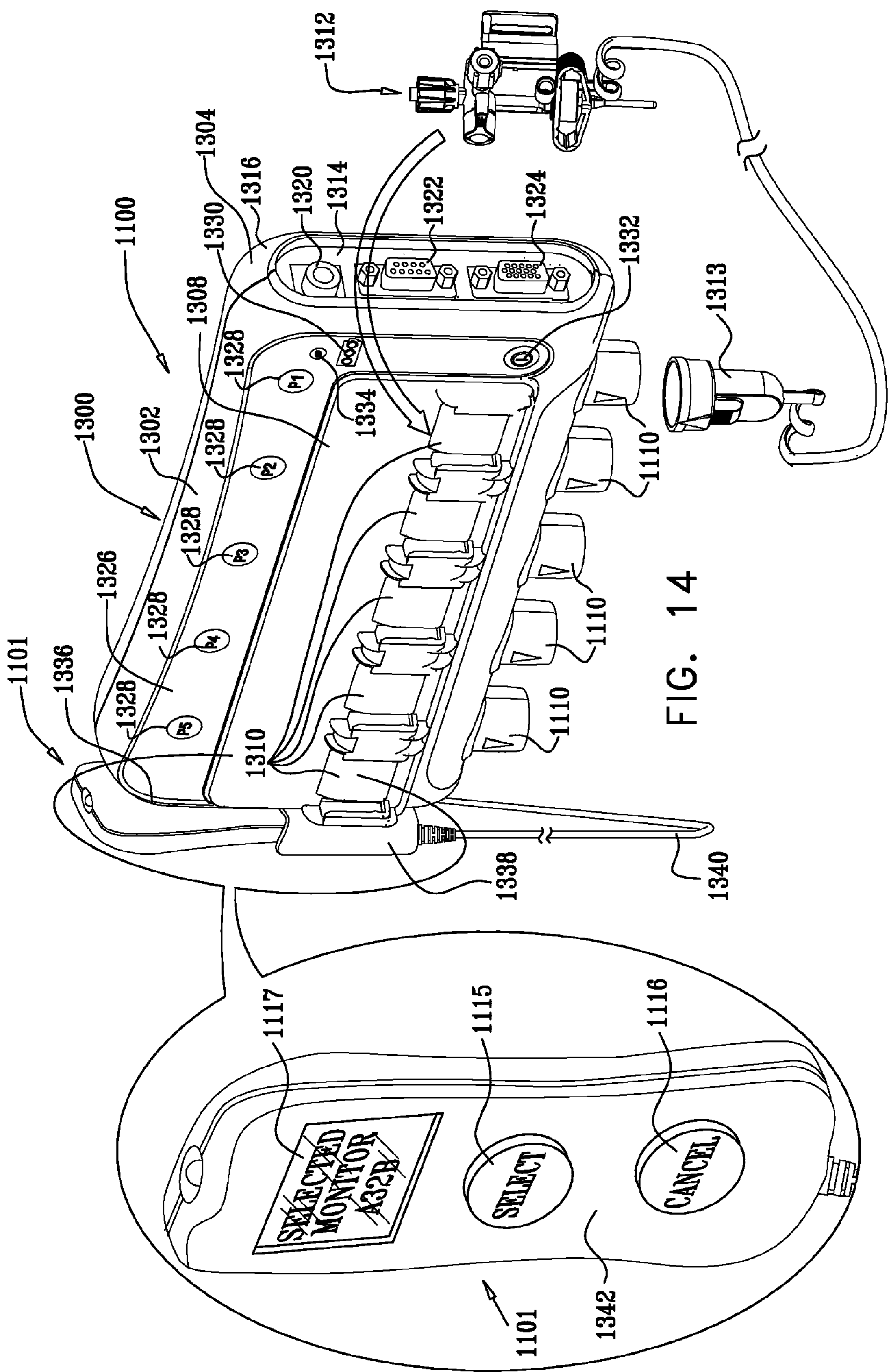
FIG. 14 is a simplified pictorial illustration of the patient companion assembly of FIGS. 11A-12C.

Reference is now made to FIG. 14, which is a simplified pictorial illustration of the patient companion assembly of FIGS. 11A-12C. As seen in FIG. 14, the patient companion assembly 1100 comprises a housing 1300, preferably composed of a forward portion 1302 and a rear portion 1304, which preferably encloses the apparatus of FIGS. 12A-12C. Mounted on a bottom edge of housing 1300 are a plurality of pressure transducer connector sockets 1110, preferably five sockets 1110, such as an RJ11 female modular jack, commercially available from Bel-Fuse of Glen Rock, Pa., USA. Each socket 1110 preferably includes a suitable pressure sensor connector (not shown) which is coupled to pressure input channel interface 1154 (FIGS. 12A-12C). A front panel 1308 preferably defines mounting attachment protrusions arranged to define a plurality of pressure transducer mounting sockets 1310, preferably five sockets 1310, which are adapted to removably support conventional blood pressure transducer assemblies 1312 each including a connector 1313, such as Transpac IT, commercially available from Elcam Medical A.C.A.L. of Kibbutz Baram, Israel, under catalog designation "fully integrated disposable blood pressure transducer".

Mounted in a recess 1314 at a side edge 1316 of housing 1300 there is preferably provided an SPO2 connector socket 1320, such as a D-Type 9S connector socket commercially available from Molex of Illinois, USA, which preferably includes a suitable SPO2 sensor connector (not shown) which is coupled to SPO2 input channel interface 1194 (FIGS. 12A-12C). At recess 1314 there is additionally provided an ECG sensor socket 1322, such as a conventional female D-Type 15S connector socket commercially available from Molex of Illinois, USA, which preferably includes a suitable ECG sensor connector (not shown) which is coupled to ECG input channel interface 1174 (FIGS. 12A-12C). Further provided at recess 1314 is a temperature sensor socket 1324, such as a conventional female RS Phone jack ¼" socket commercially available from Switchcraft Inc. of Chicago, Ill., USA, which preferably includes a suitable temperature sensor connector (not shown) which is coupled to temperature input channel interface 1204 (FIGS. 12A-12C).

Located alongside front panel 1308 is a control panel 1326 including a plurality of pressure channel control buttons 1328, preferably five buttons 1328, which control operation of the blood pressure transducer assemblies 1312. Also, preferably included in the control panel 1326 is a battery charge status indicator 1330, a power on/off button 1332 and an audio/visual alarm indicator 1334.

On side edge 1336 of the housing 1300, opposite side edge 1316, is a selector support element 1338, which seats monitor selector 1101. Monitor selector 1101 is preferably connected to the housing 1300 of patient companion assembly 1100, typically by a cable 1340. As seen in the enlarged portion of FIG. 14, the SELECT button 1115, the display 1117 and the CANCEL button 1116 are preferably provided on a front surface 1342 of monitor selector 1101.

Reference is now made to FIG. 15, which is a simplified flow chart illustration of the operation of the system of FIGS. 11A-14. As seen in FIG. 15, when the power on/off button 1332 (FIG. 14) is in a power-off state, operation of the patient companion assembly 1100 (FIGS. 11A-11B) is initiated either by an operator pressing the power on/off button 1332 or by an operator inserting the connector 1313 of a blood pressure transducer 1312 into a socket 1110 (FIG. 14). Various system checks are carried out automatically by the controller 1232 of FIGS. 12A-12C. If a problem is encountered, an alarm is preferably indicated by audio/visual indicator 1334 (FIG. 14) and the patient companion assembly power is shut down.

If no problem is encountered during the system checks, an attempt is made to establish wireless communication with digital wireless communication subsystem 1252 (FIGS. 13A and 13B) of a monitor such as monitor 1102 (FIGS. 11A-11B). The wireless transceiver 1164 of the patient companion assembly 1100 (FIGS. 12A-12C) ranks receivers in its vicinity according to the strength of a signal emitted therefrom. Typically, a predetermined number of receivers, preferably 3, are ranked.

Thereafter, an attempt is made by the digital wireless communication subsystem 1162 of the patient companion assembly 1100 to establish communication with digital wireless communication subsystem 1252 of the monitor having the highest ranking. The monitor that is being communicated with indicates the communication thereof by providing an audio/visual indication, such as a triangular waveform, for a predetermined time duration, typically 10 seconds.

If the monitor selector 1101 is directed at another monitor and the SELECT button 1115 (FIG. 14) is pressed during the predetermined time duration, an attempt is made by the digital wireless communication subsystem 1162 of the patient companion assembly 1100 to establish communication with digital wireless communication subsystem 252 of the monitor at which the monitor selector 1101 is directed.

If none of the buttons of control panel 1326 (FIG. 14) of the patient companion assembly 1100 or of monitor selector 1101 were pressed during the predetermined time duration, the patient companion assembly confirms the establishing of communication with the selected monitor.

Following confirmation, and if a sensor is connected to a socket of the patient companion assembly 1100 the selected monitor displays the sensor signals transmitted by the transmitter 1164 of the patient companion assembly 1100. If no sensor is connected to a socket of the patient companion assembly, the patient companion assembly continues in an idle state for a predetermined time duration, and if no sensor is connected during that time, the patient companion assembly power is shut down.

Alternatively, the patient companion assembly 1100 may attempt establishing communication with one of the monitors only when a sensor is connected to a suitable socket of the patient companion assembly.

If the CANCEL button 1116 is pressed, the display of sensor signals on the monitor currently displaying them is terminated, and the patient companion assembly continues in an idle state for a predetermined time duration. If an operator selects another monitor by pressing the SELECT button 1115 during the predetermined time duration an attempt is made to establish communication between the patient companion assembly and the selected monitor as described above, and if the predetermined time duration elapses and no monitor is selected the patient companion assembly power is shut down.

It is appreciated that a monitor selector of the type shown in the embodiment of FIGS. 11A-15 may be employed in the embodiments of FIGS. 1A-10. Additionally, a monitor of the type of monitor 509 shown in the embodiment of FIGS. 6A-10 may be employed in the embodiment of FIGS. 11A-15.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. An operator-controllable medical monitoring system comprising:

a plurality of medical sensors that are each adapted to sense a corresponding patient characteristic; and a patient companion assembly including:

a patient companion assembly wireless transceiver;

a medical sensor interface unit including a plurality of medical sensor interconnection ports for receiving information from at least one of said plurality of medical sensors; and a medical monitor selector for automatically selecting a first one of a plurality of medical monitors, each including a medical information display, for display of said information, said medical monitor selector including an operator controllable switch for enabling operator selection of a second one of said plurality of medical monitors for display of said information, said second one of said plurality of medical monitors being selected automatically in accordance with the strength of a wireless signal sensed by the patient companion assembly wireless transceiver, said second one of said plurality of medical monitors being different from said first one of said plurality of medical monitors.

2. The system according to claim 1, wherein said medical sensor interface unit comprises at least one of a pressure sensor interface subunit, an ECG sensor interface subunit, an SPO2 sensor interface subunit, a temperature sensor interface subunit, a blood chemistry sensor interface subunit and a respiratory parameter sensor interface subunit.

3. The system according to claim 1, wherein:

each of said plurality of medical sensor interconnection ports comprises:

a medical sensor connector operative to be coupled to a medical sensor; and a medical sensor input channel interface coupled to said medical sensor connector and including an amplifier and a filter; and said medical sensor interface unit comprises:

at least one A/D converter which is operative to convert analog medical sensor signals received from said plurality of medical sensor interconnection ports into digital medical sensor signals; and a medical sensor input processor operative to adapt said digital medical sensor signals for digital wireless communication, and to supply said digital medical sensor signals to said patient companion assembly wireless transceiver.

4. The system according to claim 1, wherein:

said patient companion assembly comprises at least one socket adapted to receive at least one corresponding sensor connector associated with said at least one of said plurality of medical sensors; and said patient companion assembly is operative to power-up upon insertion of said at least one sensor connector to said at least one socket.

5. The system according to claim 4, wherein said patient companion assembly is operative to shut-down if no sensor connector is connected to said at least one socket for a predetermined time duration.

6. The system according to claim 1, wherein said plurality of medical sensors comprises at least one of an intracranial pressure sensor, an arterial pressure sensor and a venous pressure sensor.

7. The system according to claim 1, wherein said patient companion assembly also comprises sensing circuitry operative to sense changes in electrical characteristics of said operator-controllable medical monitoring system which are indicative of the activation of said at least one of said plurality of medical sensors, and to power up said patient companion assembly upon sensing said changes.

8. The system according to claim 1 wherein said patient companion assembly is operative to transmit said information to said first one of said plurality of medical monitors for display.

9. The system according to claim 8 wherein said patient companion assembly is operative, in response to said operator controllable switch to terminate transmission of said information to said first one of said plurality of medical monitors and to transmit said information to said second one of said plurality of medical monitors for display.

10. The system according to claim 1 and also comprising at least one monitor interface assembly associated with each of said plurality of medical monitors, said at least one monitor interface assembly comprising:

a plurality of monitor interface subunits; and a monitor interface wireless transceiver, said monitor interface wireless transceiver being adapted to communicate with said patient companion assembly wireless transceiver.

11. The system according to claim 10 wherein said monitor interface assembly is adapted to be connected to a conventional medical monitor.

12. The system according claim 1, wherein each medical monitor of said plurality of medical monitors comprises at least one sensor socket operative to provide electrical power obtained from said medical monitor to at least one of said monitor wireless transceiver and electrical circuitry coupled to other sensor sockets.

13. The system according claim 1, wherein said patient companion assembly is operative automatically to establish communication between said plurality of medical sensors and said first one of said plurality of medical monitors, absent operator intervention.

14. A method for operator-controllable medical monitoring of a patient comprising:

employing at least one medical sensor that is adapted to sense at least one patient characteristic;

receiving information from said at least one medical sensor;

automatically selecting a first one of a plurality of medical monitors to display said information;

establishing communication between said at least one medical sensor and said first one of said plurality of medical monitors;

displaying said information on said first one of said plurality of medical monitors;

manually selecting to display said information on an alternative one of said plurality of medical monitors;

automatically selecting a second one of said plurality of medical monitors in accordance with a strength of a wireless signal sensed by a patient companion assembly wireless transceiver; and subsequent to said automatically selecting:

terminating display of said information on said first one of said plurality of medical monitors; and displaying said information on said second one of said plurality of medical monitors.

15. The method according to claim 14 further comprising, employing sensing circuitry forming part of said patient companion assembly to sense changes in electrical characteristics which are indicative of the activation of said at least one medical sensor, and to power up said patient companion assembly upon sensing said changes.

16. The method according to claim 14 further comprising employing power management functionality, operative, upon insertion of at least one sensor connector to at least one socket of a monitor, to power-up said patient companion assembly.

17. The method according to claim 16 further comprising, employing said power management functionality to shut-down said patient companion assembly if a sensor connector is not connected to said at least one socket for a predetermined time duration.

* * * * *